United States Patent
Guo

(10) Patent No.: US 9,933,431 B2
(45) Date of Patent: Apr. 3, 2018

(54) SYSTEM AND METHOD FOR ITERATIVE DETECTION OF BIOLOGICAL MOLECULES

(71) Applicant: Jia Guo, Tempe, AZ (US)

(72) Inventor: Jia Guo, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/820,875

(22) Filed: Aug. 7, 2015

(65) Prior Publication Data

US 2016/0054308 A1 Feb. 25, 2016

Related U.S. Application Data

(60) Provisional application No. 62/040,678, filed on Aug. 22, 2014.

(51) Int. Cl.
*C12Q 1/68* (2006.01)
*G01N 33/58* (2006.01)

(52) U.S. Cl.
CPC ......... *G01N 33/582* (2013.01); *C12Q 1/6823* (2013.01)

(58) Field of Classification Search
CPC .......................... G01N 33/582; C12Q 1/6823
USPC .......................................... 435/6.1; 536/26.6
See application file for complete search history.

(56) References Cited

U.S. PATENT DOCUMENTS

| | | | |
|---|---|---|---|
| 6,150,173 A | 11/2000 | Schubert et al. | |
| 7,414,116 B2 | 8/2008 | Milton et al. | |
| 7,741,045 B2 | 6/2010 | Gerdes et al. | |
| 8,354,231 B2 | 1/2013 | Kwong et al. | |
| 9,175,342 B2 * | 11/2015 | Ju ........................ | C07H 19/06 |
| 2006/0160081 A1 * | 7/2006 | Milton .................. | C07H 19/06 |
| | | | 435/6.12 |
| 2010/0009364 A1 | 1/2010 | Fantl et al. | |
| 2011/0263457 A1 | 10/2011 | Krutzik et al. | |

FOREIGN PATENT DOCUMENTS

| | | |
|---|---|---|
| WO | 2009/051807 | 4/2009 |
| WO | 2009/054922 | 4/2009 |

OTHER PUBLICATIONS

Bendall, S. C.; Nolan, G. P. Nat. Biotechnol. 2012, 30, 639.
Bendall, S. C.; Simonds, E. F.; Qiu, P.; Amir, E. D.; Krutzik, P. O.; Finck, R.; Bruggner, R. V; Melamed, R.; Trejo, A.; Ornatsky, O. I.; Balderas, R. S.; Plevritis, S. K.; Sachs, K.; Pe'er, D.; Tanner, S. D.; Nolan, G. P. Science 2011, 332, 687.
Bodenmiller, B.; Zunder, E. R.; Finck, R.; Chen, T. J.; Savig, E. S.; Bruggner, R. V; Simonds, E. F.; Bendall, S. C.; Sachs, K.; Krutzik, P. O.; Nolan, G. P. Nat. Biotechnol. 2012, 30, 858.
Ma, C.; Fan, R.; Ahmad, H.; Shi, Q.; Comin-Anduix, B.; Chodon, T.; Koya, R. C.; Liu, C.-C.; Kwong, G. a; Radu, C. G.; Ribas, A.; Heath, J. R. Nat. Med. 2011, 17, 738.
Wei, W.; Shi, Q.; Remacle, F.; Qin, L.; Shackelford, D. B.; Shin, Y. S.; Mischel, P. S.; Levine, R. D.; Heath, J. R. Proc. Natl. Acad. Sci. U. S. A. 2013, 110, E1352.
Shi, Q.; Qin, L.; Wei, W.; Geng, F.; Fan, R.; Shin, Y. S.; Guo, D.; Hood, L.; Mischel, P. S.; Heath, J. R. Proc. Natl. Acad. Sci. U. S. A. 2012, 109, 419.
Guo, J.; Wang, S.; Dai, N.; Teo, Y. N.; Kool, E. T. Proc. Natl. Acad. Sci. U. S. A. 2011, 108, 3493.
Schubert, W.; Bonnekoh, B.; Pommer, A. J.; Philipsen, L.; Böckelmann, R.; Malykh, Y.; Gollnick, H.; Friedenberger, M.; Bode, M.; Dress, A. W. M. Nat. Biotechnol. 2006, 24, 1270.
Gerdes, M. J.; Sevinsky, C. J.; Sood, A.; Adak, S.; Bello, M. O.; Bordwell, A.; Can, A.; Corwin, A.; Dinn, S.; Filkins, R. J.; Hollman, D.; Kamath, V.; Kaanumalle, S.; Kenny, K.; Larsen, M.; Lazare, M.; Li, Q.; Lowes, C.; McCulloch, C. C.; McDonough, E.; Montalto, M. C.; Pang, Z.; Rittscher, J.; Santamaria-Pang, A.; Sarachan, B. D.; Seel, M. L; Seppo, A.; Shaikh, K.; Sui, Y.; Zhang, J.; Ginty, F. Proc. Natl. Acad. Sci. U. S. A. 2013, 110, 11982.
Micheva, K. D.; Smith, S. J. Neuron 2007, 55, 25.
Micheva, K. D.; Busse, B.; Weiler, N. C.; O'Rourke, N.; Smith, S. J. Neuron 2010, 68, 639.
Zrazhevskiy, P.; Gao, X. Nat. Commun. 2013, 4, 1619.
Schweller R. M.; Zimak, J.; Duose, D. Y.; Qutub, A. a; Hittelman, W. N.; Diehl, M. R. Angew. Chem. Int. Ed. Engl. 2012, 51, 9292.
Duose, D. Y.; Schweller, R. M.; Zimak, J.; Rogers, A. R.; Hittelman, W. N.; Diehl, M. R. Nucleic Acids Res. 2012, 40, 3289.
Duose, D. Y.; Schweller, R. M.; Hittelman, W. N.; Diehl, M. R. Bioconjug. Chem. 2010, 21, 2327.
Giesen, C.; Wang, H. a O.; Schapiro, D.; Zivanovic, N.; Jacobs, A.; Hattendorf, B.; Schüffler, P. J.; Grolimund, D.; Buhmann, J. M.; Brandt, S.; Varga, Z.; Wild, P. J.; Günther, D.; Bodenmiller, B. Nat. Methods 2014, 11, 417.
Angelo, M.; Bendall, S. C.; Finck, R.; Hale, M. B.; Hitzman, C.; Borowsky, A. D.; Levenson, R. M.; Lowe, J. B.; Liu, S. D.; Zhao, S.; Natkunam, Y.; Nolan, G. P. Nat. Med. 2014, 20, 436.
Guo, J.; Yu, L.; Turro, N. J.; Ju, J. Acc. Chem. Res. 2010, 43, 551.
Franzini, R. M.; Kool, E. T. J. Am. Chem. Soc. 2009, 131, 16021.
Buus, et al., Mol. Cell. Proteomics 2012, 11, 1790.
Dai, N.; Guo, J.; Teo, Y. N.; Kool, E. T. Angew. Chem. Int. Ed. Engl. 2011, 50, 5105.
Wang, S.; Guo, J.; Ono, T.; Kool, E. T. Angew. Chemie Int. Ed. 2012, 51, 7176.
Garini, Y.; Young, I. T.; McNamara, G. Cytometry. A 2006, 69, 735.
Leriche, et al., Bioorg. Med. Chem., 2012, 20, 571-582.

\* cited by examiner

*Primary Examiner* — Jezia Riley

(74) *Attorney, Agent, or Firm* — Quarles & Brady LLP

(57) ABSTRACT

A system for the iterative detection of biological molecules includes a probe, and a fluorophore tethered to the probe with an azide-based linker. The linker is configured to be cleaved in the presence of tris(2-carboxyethyl)phosphine (TCEP), and the on/off ratio between a signal measured before treatment with TCEP and a signal measured after treatment with TCEP is at least about 20:1.

9 Claims, 16 Drawing Sheets

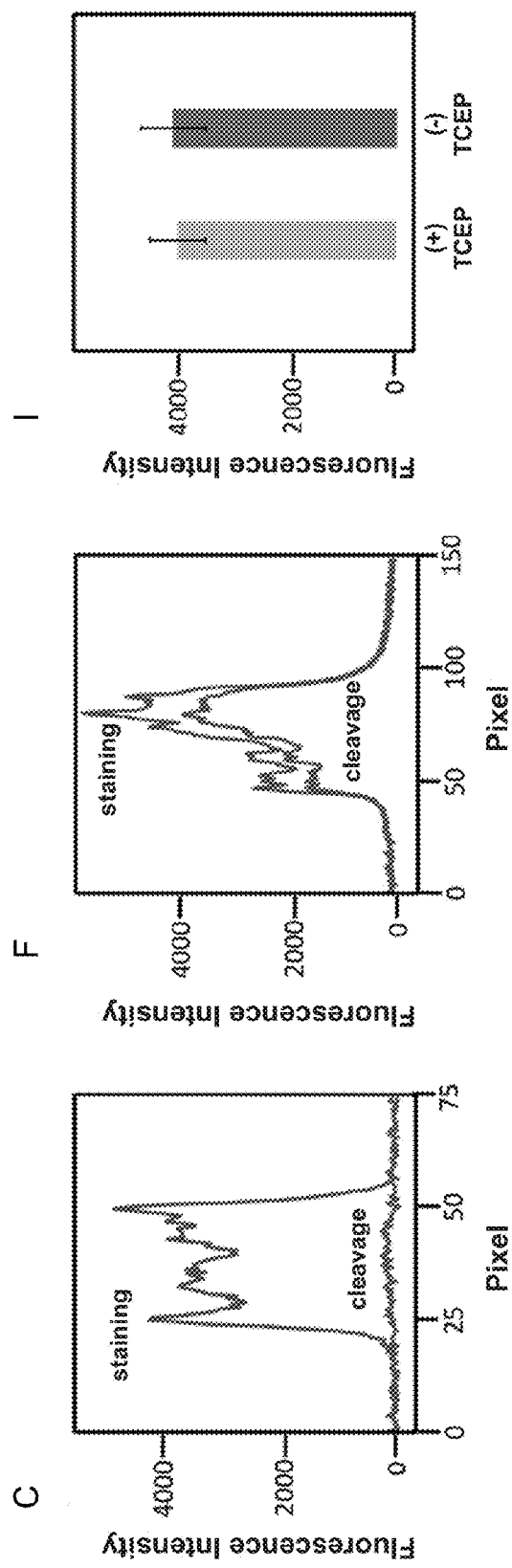
Figures 5A-5I, CONTINUED

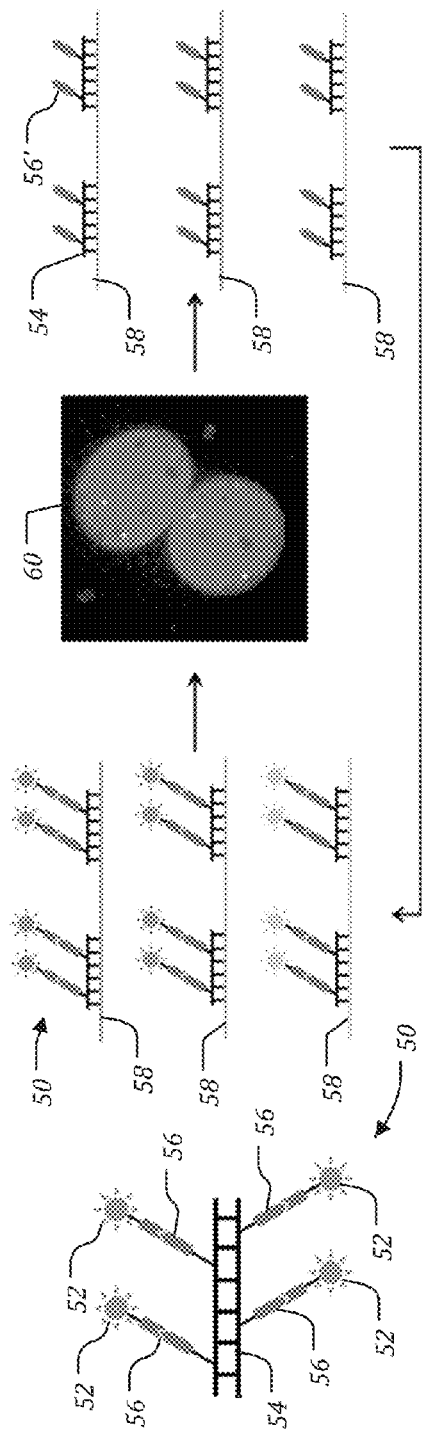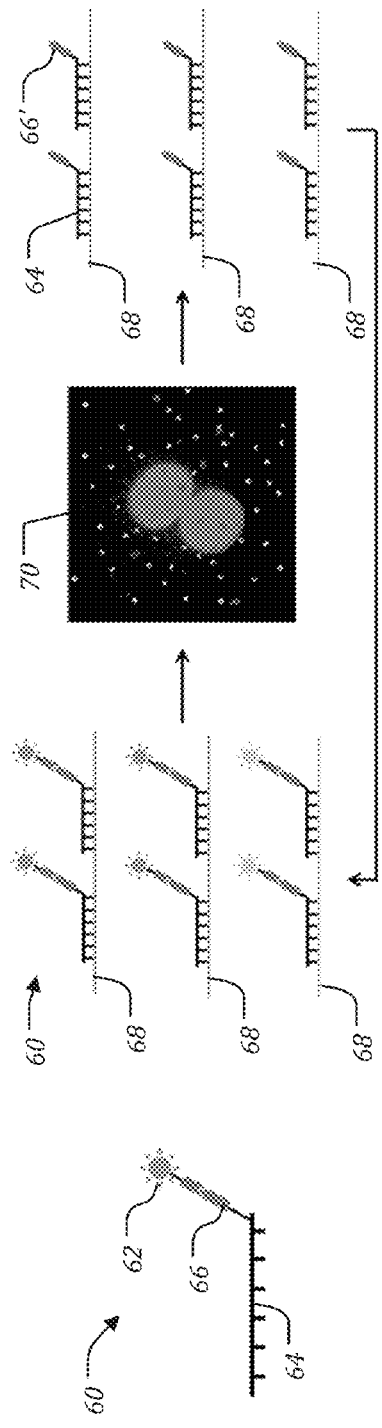

SYSTEM AND METHOD FOR ITERATIVE DETECTION OF BIOLOGICAL MOLECULES

CROSS-REFERENCE TO RELATED APPLICATIONS

This application claims priority to U.S. Provisional Appn. No. 62/040,678 filed Aug. 22, 2014, which is hereby incorporated by reference herein for all purposes.

STATEMENT REGARDING FEDERALLY SPONSORED RESEARCH

Not applicable.

BACKGROUND OF THE INVENTION

The disclosure relates, in general, to the iterative detection of biological molecules and, more particularly, to cleavable linkers for tethering detectable moieties to biological probes.

Fluorescence imaging is a pervasive technique in the fields of chemistry, biology, medicine and so forth. For example, comprehensive protein profiling on the single-cell level may be useful to understand complex molecular pathways in heterogeneous cell populations (Bendall, et al., Nat. Biotechnol. 2012, 30, 639; Bendall, et al., Science 2011, 332, 687; Bodenmiller, et al., Nat. Biotechnol. 2012, 30, 858; Ma, et al., Nat. Med. 2011, 17, 738; Wei, et al., Proc. Natl. Acad. Sci. U.S.A. 2013, 110, E1352; Shi, et al., Proc. Natl. Acad. Sci. U.S.A. 2012, 109, 419). Immunofluorescence microscopy has been widely used to quantify the identities, positions and abundances of proteins in individual cells. Therefore, it may be well-suited for analyzing cell heterogeneity and the spatial complexity of proteins. Similarly, fluorescence based detection schemes have been developed for DNA and RNA-based targets. However, due to the spectral overlap of commonly available fluorophores, the capacity of conventional immunofluorescence techniques can be limited (Guo, J. et al., Proc. Natl. Acad. Sci. U.S.A. 2011, 108, 3493).

Various techniques have been developed to address limitations of conventional fluorescence imaging techniques and enable more comprehensive DNA, RNA and protein analysis. One class of techniques includes multiplex or iterative immunofluorescence with continuous cycles of staining, imaging, and fluorescence signal erasing. Example methods used for iterative immunofluorescence may rely on photobleaching (Schubert, et al., Nat. Biotechnol. 2006, 24, 1270), chemical reagents (Gerdes, et al., Proc. Natl. Acad. Sci. U.S.A. 2013, 110, 11982; Micheva, et al., Neuron 2007, 55, 25; Micheva, et al., Neuron 2010, 68, 639; Zrazhevskiy, et al., Nat. Commun. 2013, 4, 1619) or DNA displacement reactions (Schweller, et al., Angew. Chem. Int. Ed. Engl. 2012, 51, 9292; Duose, et al., Nucleic Acids Res. 2012, 40, 3289; Duose, et al., Bioconjug. Chem. 2010, 21, 2327) to photobleach fluorophores, chemically inactivate fluorophores, remove fluorescent antibodies or disassemble fluorescent DNA complexes.

While each of the aforementioned methods may offer advantages over conventional fluorescence imaging techniques, a number of limitations remain. In one aspect, partial photobleaching during the imaging process and incomplete fluorescence signal removal after bleaching may hinder the consistent quantification of protein abundances. In another aspect, harsh chemical reagents often result in specimen degradation and interfere with subsequent cycles of staining. In a further aspect, mis-hybridization between different DNA complexes along with non-specific binding between DNA complexes and endogenous biomolecules may lead to increased background. Recently, mass cytometry imaging (Giesen, et al., Nat. Methods 2014, 11, 417) and ion beam imaging (Angelo, et al., Nat. Med. 2014, 20, 436) with metal isotope labeled antibodies have been developed for protein profiling. However, these mass spectrometry based approaches may have limited imaging resolution or imaging speed and sample throughput. Accordingly, there is a need for fluorescence imaging techniques that overcome the aforementioned limitations.

SUMMARY OF THE INVENTION

The present invention overcomes the aforementioned drawbacks by providing a system and method for the iterative detection of biological molecules. In accordance with one aspect of the present disclosure, a system for the iterative detection of biological molecules includes a probe, and a fluorophore tethered to the probe with an azide-based linker. The linker is configured to be cleaved in the presence of tris(2-carboxyethyl)phosphine (TCEP), and the on/off ratio between a signal measured before treatment with TCEP and a signal measured after treatment with TCEP is at least about 20:1.

In accordance with another aspect of the present disclosure, a method of detecting a biological molecule includes incubating a sample including a target molecule with a detection system. The detection system includes a probe and a fluorophore tethered to the probe with an azide-based linker. The method further includes exciting the sample at a first wavelength, detecting the emission of a second wavelength from the sample, and treating the sample with tris(2-carboxyethyl)phosphine, thereby cleaving the fluorophore from the probe.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A is a fluorescence image of microtubules labeled with cleavable fluorescent antibodies. FIG. 5B is a fluorescence image after fluorophores were removed by cleavage of the linker using TCEP. FIG. 5C is a fluorescence intensity profile corresponding to white lines A and B in FIGS. 5A and 5B, respectively. FIG. 5D is a fluorescence image of microtubules are labeled with conventional fluorescent antibodies, and FIG. 5E is a fluorescence image of the system shown in 5F following incubation with TCEP. FIG. 5F is a fluorescence intensity profile corresponding to white lines D and E in 5D and 5E, respectively. FIG. 5G is a fluorescence image of microtubules stained with cleavable fluorescent antibodies after incubation with TCEP for 24 hours. FIG. 5H is a fluorescence image of microtubules directly stained with cleavable fluorescent antibodies without incubation with TCEP. FIG. 5I is a plot of fluorescence intensity of the microtubules staining in 5G and 5H. Scale bars in FIGS. 5A, 5B, 5D, 5E, 5G and 5I represent 20 μm.

FIG. 8 is a schematic illustration of multiplexed RNA FISH with cleavable fluorescent probes. RNAs in fixed cells may be hybridized with cleavable fluorescent oligonucleotides. After imaging, the fluorophores may be removed by cleavage of the linker. Through cycles of staining, imaging and cleavage, a large number of different RNAs may be quantified in individual cells.

FIG. 9 is a schematic illustration of multiplexed DNA FISH with cleavable fluorescent probes. Different genomic regions in fixed cells may be hybridized with cleavable fluorescent PCR products. After imaging, the fluorophores may be removed by cleavage of the linker. Through cycles of staining, imaging and cleavage, a large number of different genomic regions may be quantified in individual cells.

FIG. 10A is a fluorescence image of spots corresponding to single mRNA molecules resulting from the transcription of the gene GAPDH. FIG. 10B is a fluorescence image showing fluorescence signal removal to facilitate the detection of different mRNA in subsequent cycles. FIG. 10C is a fluorescence image of spots corresponding to single mRNA molecules resulting from the transcription of the gene ACTB. Scale bars in FIGS. 10A-10C represent 10 μm.

FIG. 19A is a fluorescence image of Ki67 antibodies labeled with antibodies conjugated to azido-azido-TAMRA. FIG. 19B is a fluorescence image showing fluorophores removed by cleavage of the linker using TCEP. FIG. 19C is a fluorescence intensity profile corresponding to white lines A and B in FIGS. 19A and 19B, respectively.

Like numbers will be used to describe like parts from Figure to Figure throughout the following detailed description.

DETAILED DESCRIPTION OF THE INVENTION

Figure 1:
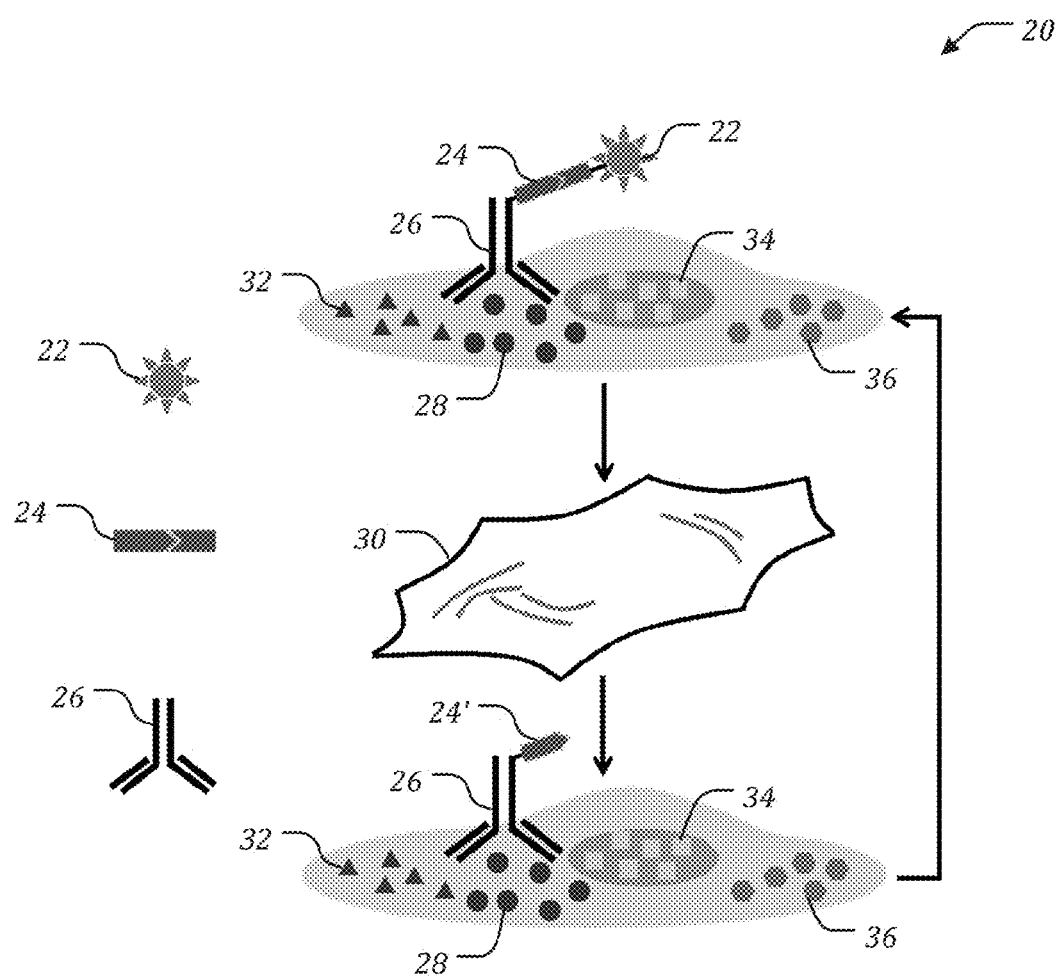
FIG. 1 is a schematic illustration of iterative immunofluorescence using chemically cleavable fluorescent antibodies. Molecular targets in fixed cells may be recognized by antibodies tethered to fluorophores through a chemically cleavable linker. After imaging, the fluorophores may be removed by chemical cleavage of the linker. Through cycles of staining, imaging and cleavage, a large number of different molecular targets may be detected in individual cells.

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention.

As also discussed above, in various situations it may be useful to provide a system and method for the detection of a biological target, such as RNA, DNA, protein or small molecules. For example, it may be useful to detect the presence of a biological target with a probe linked to a detectable marker. Accordingly, the probe may be used to selectively bind or otherwise interact with the biological target while the linked marker may be detected using various techniques. However, many systems and methods for the detection of a biological target may be limited to the detection of only a small number (e.g., <5) targets for a given sample. In one aspect, the binding of the target molecule to the probe may not be reversible thereby preventing the reuse of a given detectable marker. In another aspect, if the binding of the target molecule to the probe is reversible, the mechanism by which the reversible binding is controlled (e.g., cleavage of the detectable marker from the probe) may perturb the sample being probed. Various other problems may also arise as the complexity of a given sample grows or as the requirements for the detection limit becomes more exacting.

Use of the disclosed system and method may address these and other issues. In one example, a probe may be coupled or tethered to a detectable marker with a cleavable linker. The probe may be used to bind or otherwise interact with a given biological target while the detectable maker may be used to determine the presence (or absence) of the biological target in a quantitative or qualitative manner. The linker may be cleavable using a variety of approaches including the addition of a chemical agent, irradiation with one or more wavelengths of light, enzymatic reaction and the like. Accordingly, following an initial round of binding and detection, the linker may be cleaved, thereby separating the detectable marker from the probe. Thereafter, the detectable marker may be inactivated or removed from the sample including the biological target such that additional rounds of binding and detection may be carried out use the same (or similar) detectable markers.

In one aspect, the cleavage mechanism may be selected such that there are little to no detrimental affects on the sample being probed. For example, one or more of the probe, linker, detectable marker and cleavage mechanism may be selected to be biocompatible. Therefore, the present system and method may be used for the iterative detection of biological molecules without substantially altering the sample or substantially affecting the results or data collected in subsequent rounds of detection.

In general, the present disclosure provides fluorescence techniques that may overcome one or more of the aforementioned limitations of conventional techniques in order to enable more comprehensive DNA, RNA and protein analysis. In one aspect, the disclosure provides for a cyclical fluorescence detection using cleavable fluorescent probes including antibodies for protein detection and oligonucleotides for DNA and RNA detection. The approach may be able to quantify over one hundred different targets at the optical resolution in single cells. In each fluorescence detection cycle, probes tethered to fluorophores through a chemically cleavable linker may be used to quantify a corresponding molecular target. After fluorescence imaging and data storage, the fluorophores attached to the probes may be efficiently removed by chemical cleavage of the linker. Subsequently, varied probes labeled with the same cleavable fluorophore may be added to the sample to analyze corresponding molecular targets. After continuous cycles of target binding, fluorescence imaging and fluorophore cleavage, a comprehensive profiling of DNA, RNA, protein, or a combination thereof, may be achieved in single cells.

With reference to FIG. 1, an embodiment of a system 20 for iterative immunofluorescence using chemically cleavable fluorescent antibodies can include a fluorophore 22, a cleavable linker 24 and an antibody 26. As shown at the top of FIG. 1, the linker 24 may be used to tether the fluorophore 22 to the antibody 26. Tethering can include a chemical or physical bond between the fluorophore 22 and the linker 24, and between the linker 24 and the antibody 26. In one aspect, the antibody 26 may selectively bind a particular population 28 of protein targets in a cell 30. Following binding of the antibody 26 to members of the population 28, fluorescence imaging may be performed on the cell 30 in order to detect the population 28. Quantitative or qualitative analysis of the population 28 in the cell 30 may be facilitated by the presence of the fluorophore 22 linked to the antibody 26 by the linker 24. Following fluorescence imaging, the linker 24 may be chemically treated, thereby cleaving the fluorophore 22 from the antibody 26. As shown at the bottom of FIG. 1, a portion 24' of the linker 24 may remain tethered to the antibody 26 following cleavage. As indicated by the arrows in FIG. 1, successive rounds of target binding, imaging and cleavage may be performed on other target protein populations within the cell 30, such as population 32, population 34 and population 36.

In some embodiments, it may be useful for an iterative immunofluorescence method to efficiently erase fluorescence signals after imaging. Furthermore, it may be useful to minimize the effects of a signal erasing step on subsequent target antigenicity. Azide-based chemically cleavable linkers have been previously used in DNA sequencing (Guo, et al., Acc. Chem. Res. 2010, 43, 551) and RNA detection Franzini, et al., Am. Chem. Soc. 2009, 131, 16021). However, DNA sequencing experiments performed by Guo et al. were carried out in a cell-free environment. Moreover, the linkers were not associated with an oligonucleotide or antibody probe. With respect to RNA detection experiments performed by Franzini, et al., cleavage of the linker was used to activate fluorescence based on fluorescence resonance energy transfer (FRET). Furthermore, the methods of Franzini et al. cannot be performed in an iterative manner. Accordingly, little evidence is available based on previous experiments as to the efficacy of azide-based chemically cleavable linkers for the detection of a target molecule in the context of either a cellular environment, or an iterative detection method.

Figure 2:
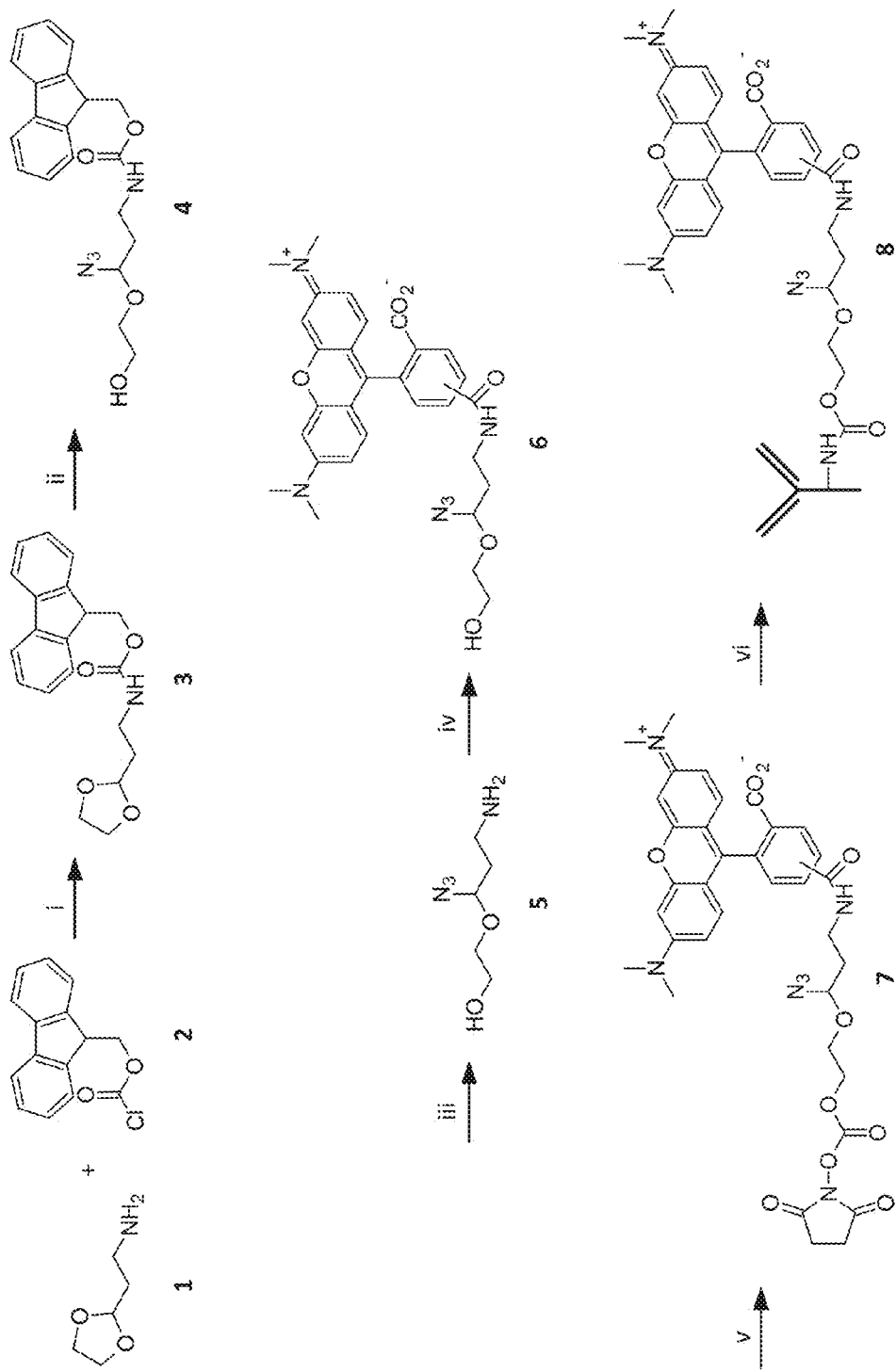
FIG. 2 is a scheme for the chemical synthesis of cleavable TAMRA conjugated antibodies.

In one aspect, the inventors have made the surprising discovery that conditions exist in which azide-based chemically cleavable linkers are compatible for use in a cellular environment for the iterative detection of a target molecule with a fluorescent probe. In some embodiments, an azide-based chemically cleavable linker may be treated with tris(2-carboxyethyl)phosphine (TCEP). It has been determined that TCEP may provide a high cleavage efficiency. Moreover, cleavage conditions used with TCEP may be generally compatible with biomolecules such as DNA, RNA, proteins and other cellular components. To test the efficacy of a TCEP cleavable linker, an example system including cleavable fluorescent antibodies with fluorophores tethered to the lysine residues through an azide-based linker were designed and synthesized as illustrated in FIG. 2. A cleavable linker 5 was synthesized in three steps. In a first step indicated by reaction arrow i, 2-(aminoethyl)-1,3-dioxolane was protected with a fluorenylmethyloxycarbonyl (Fmoc) group 2 to provide a carbamate 3. Treatment with azidetrimethylsilane and tin tetrachloride converted carbamate 3 to compound 4 as indicated by reaction arrow ii. After deprotection of the amino group in 4 with piperidine (reaction arrow iii), the cleavable linker 5 was produced. Coupling 5 with carboxytetramethylrhodamine (TAMRA) N-hydroxysuccinimide (NHS) ester yielded compound 6 (reaction arrow iv), which was subsequently converted to its corresponding NHS ester 7 by treatment with N,N'-disuccinimidyl carbonate (DSC) and triethylamine (reaction arrow v). Compound 7 was coupled with the lysine residues on antibodies to afford the cleavable TAMRA conjugated antibodies 8 as indicated by reaction arrow vi.

Figure 3:
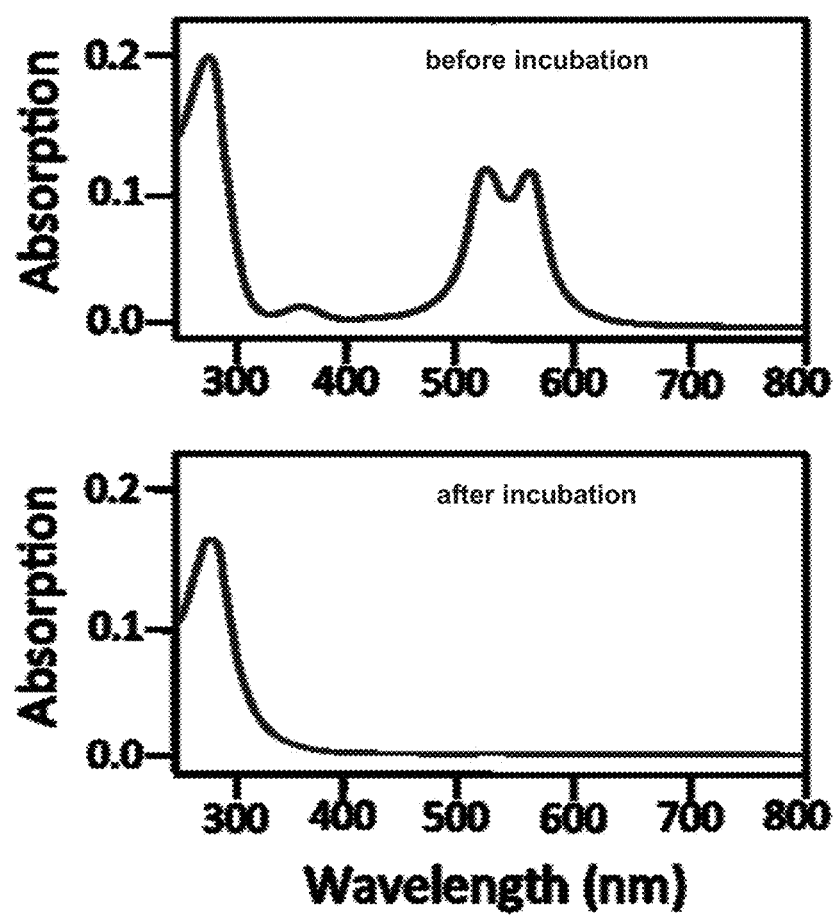
FIG. 3 is an absorption spectra of cleavable TAMRA conjugated antibodies before (top) and after (bottom) incubation with TCEP.
Figure 4:
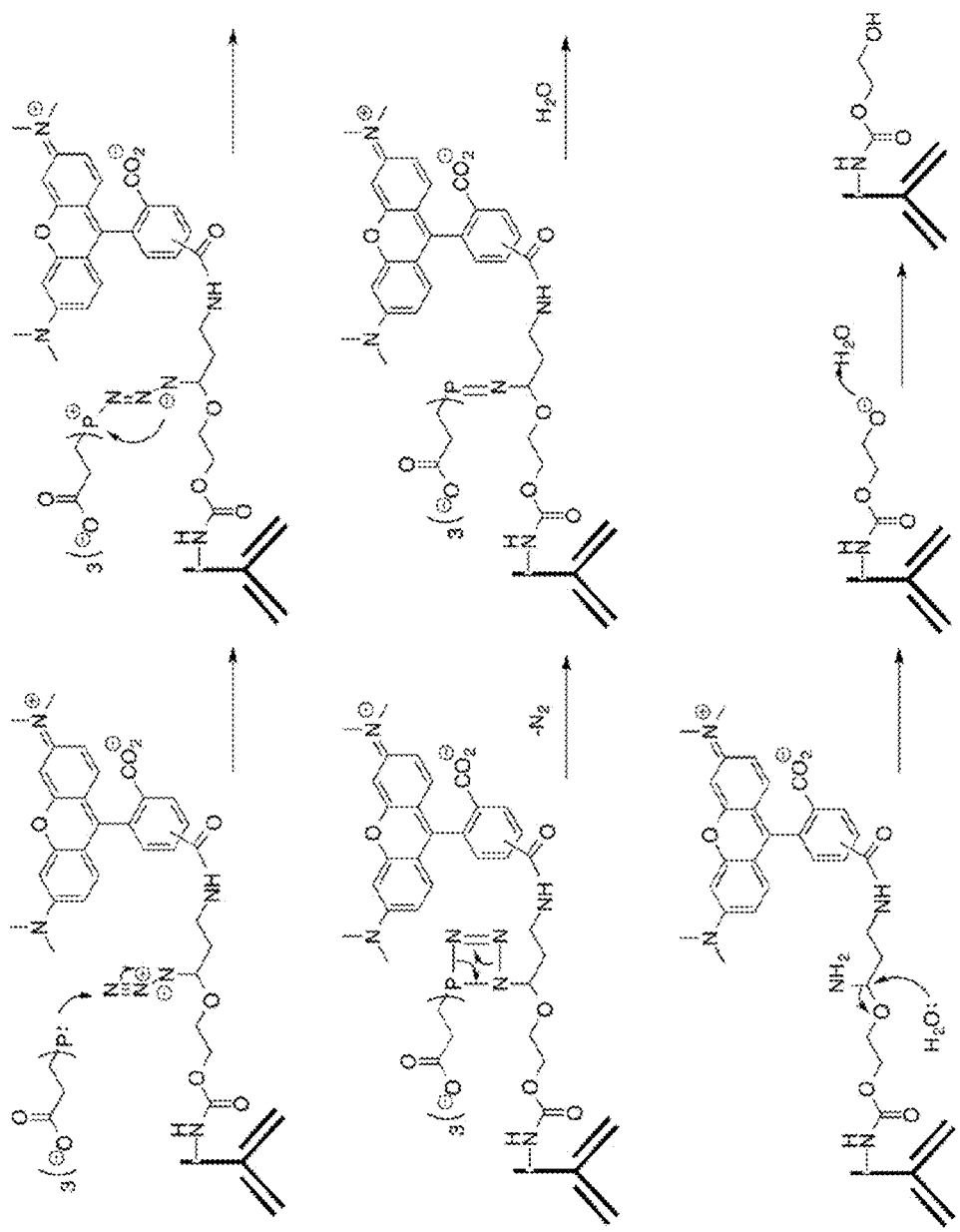
FIG. 4 is an illustration of a mechanism for the cleavage of TAMRA from antibodies using Staudinger reaction with TCEP.

TAMRA conjugated antibodies 8 were characterized by absorption spectroscopy as shown in FIG. 3. In the absorption spectrum, the peaks centered at 280 nm and 520 nm along with 560 nm correspond to antibodies and TAMRA, respectively. From the absorption spectrum, the labeling number of TAMRA per antibody was calculated to be about 2.2. These results indicate that TAMRA were successfully conjugated to antibodies through the azide-based cleavable linker. To assess the fluorophore cleavage efficiency, the labeled antibodies were incubated with 100 mM TCEP at 37° C. for 30 minutes. The azide group on the cleavable linker was reduced by TCEP via the Staudinger reaction. The following hydrolysis broke the linker and separated the fluorophores and antibodies as shown in FIG. 4.

Referring again to FIG. 3, after removing cleaved fluorophores with size exclusion chromatography, the cleavage product was characterized with absorption spectroscopy. The TAMRA peaks completely disappeared and the antibodies peak remained as a sole dominant peak. These results established that that TCEP may efficiently cleave the azide-based linker and remove the fluorophores from antibodies.

Figures 5A, 5B, 5C, 5D, 5E, 5F, 5G, 5H, 5I:
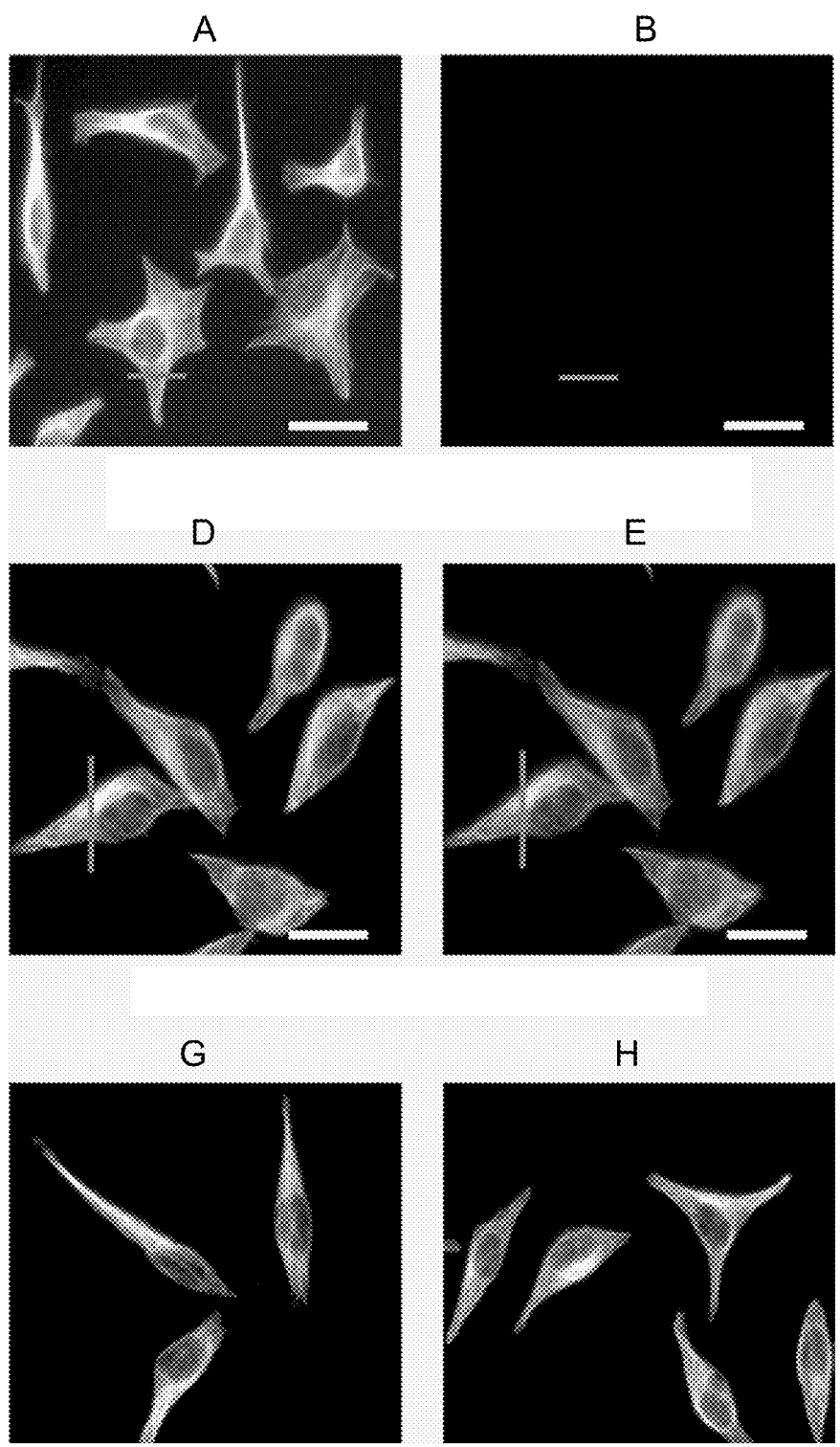
FIGS. 5A-5I show the results of iterative fluorescence detection of protein in whole cells.

To demonstrate the feasibility of performing iterative cycles of immunofluorescence with cleavable fluorescent antibodies, microtubules were labeled by targeting α-tubulin. HeLa cells were stained with rat anti-α-tubulin, and subsequently incubated with cleavable TAMRA conjugated goat anti-rat Immunoglobulin G (IgG) as shown in FIG. 5A. After fluorophore cleavage with 100 mM TCEP at 37° C. for 30 minutes, almost all of the fluorescence signal from the labeled microtubules was erased (FIG. 5B). The on/off ratio between the fluorescence signal before and after the TCEP treatment was greater than 20:1 (FIG. 5C). Control experiments were performed by staining microtubules with standard immunofluorescence (FIG. 5D). The labeling specificity and efficiency were similar to those using cleavable fluorescent antibodies. Upon TCEP treatment, the fluorescence intensities remained largely unchanged (FIG. 5E), with an on/off ratio of about 1.2:1 (FIG. 5F). These results indicated that cleavable fluorescent antibodies may recognize their targets similarly to standard fluorescent antibodies, and the immunofluorescence signal may be efficiently erased using TCEP by removing the fluorophores attached to antibodies through cleavage of the azide-based linker.

The binding site on an antigen, which is recognized by the corresponding antibody, may be generally composed of about 4 to about 12 amino acids (Buus, et al., Mol. Cell. Proteomics 2012, 11, 1790). Many commercially available antibodies are prepared by immunizing animals with synthetic peptides, whose primary sequences are used to identify antigens with antibodies. In general, the TCEP treatment does not alter the chemical structures of these peptides. Thus, the antigenicity of those protein targets may not be affected by TCEP. Even though some antigens are recognized by the three-dimensional conformation of the 4 to 12 amino acid recognition site in discontinuous primary sequences, TCEP may still not significantly change this conformation since the protein structure may be fixed by formaldehyde used in a cell fixation step. Therefore, the TCEP treatment should not interfere with the subsequent cycles of immunofluorescence staining. To demonstrate the affect (or lack thereof) of TCEP over several rounds of immunofluorescent staining, HeLa cells were incubated with (FIG. 5G) and without (FIG. 5H) TCEP at 37° C. for 24 hours, followed by microtubule labeling. The labeling specificity and the fluorescence signal intensity (FIG. 5I) were similar for both conditions tested, suggesting that the TCEP treatment does not affect the antigenicity of protein targets in subsequent immunofluorescence cycles.

Figures 6A, 6P:
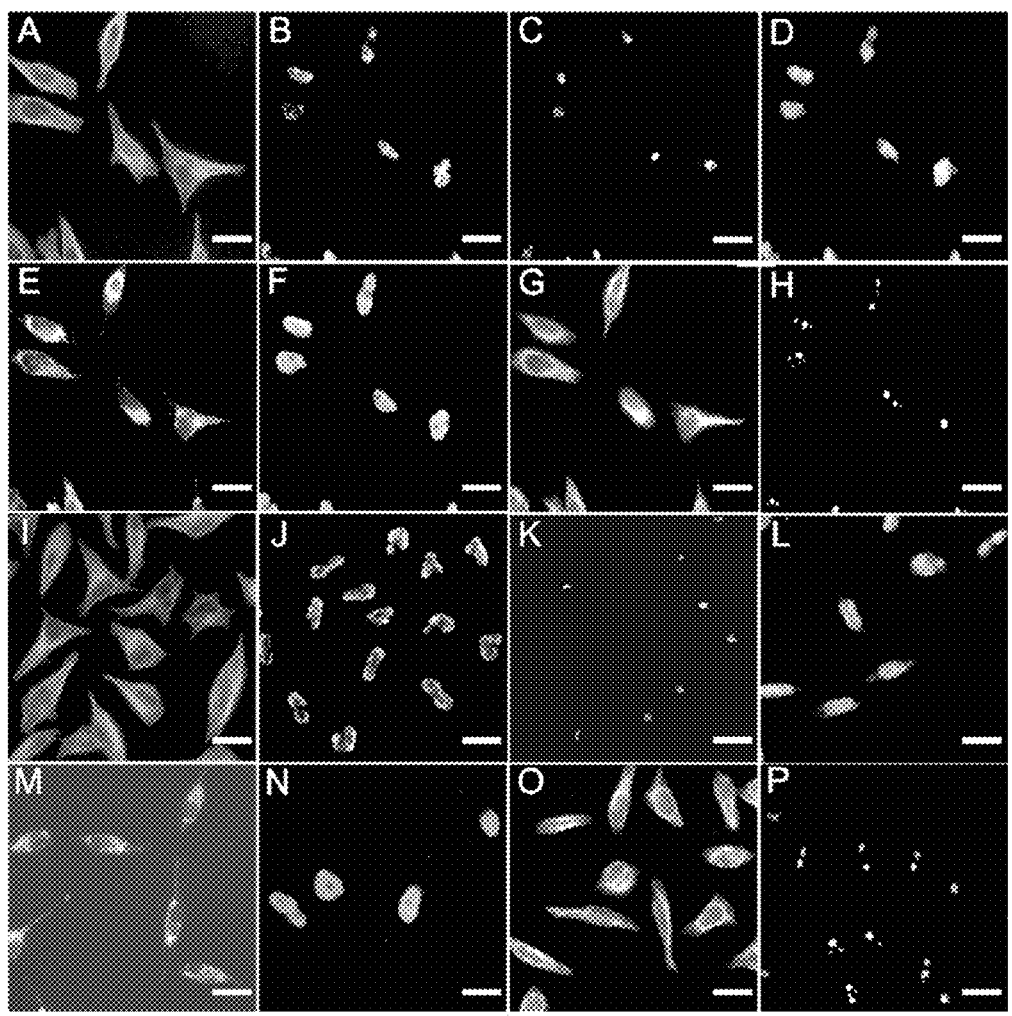
FIGS. 6A-6P are optical fluorescence images illustrating iterative fluorescence detection of protein in whole cells. (panel A) α-Tubulin, (panel B) XRCC1, (panel C) golgin-97, (panel D) TFIIH, (panel E) OxPhos complex V inhibitor protein, (panel F) nuclear antigens, (panel G) vimentin and (panel H) nucleolin are detected by cyclical immunofluorescence with cleavable fluorescent antibodies in individual cells. (panel I) α-Tubulin, (panel J) XRCC1, (panel K) golgin-97, (panel L) TFIIH, (panel M) OxPhos complex V inhibitor protein, (panel N) nuclear antigens, (panel O) vimentin and (panel P) nucleolin are stained with conventional fluorescent antibodies as controls. Scale bars in each of the panels represent 20 μm.

To assess the effectiveness of quantifying multiple proteins in single cells with cleavable fluorescent antibodies, eight different molecular targets were labeled in sequential rounds of immunofluorescence. In a first cycle, α-tubulin was stained with rat anti-α-tubulin, followed by cleavable TAMRA conjugated goat-anti-rat IgGs (FIG. 6, panel A). After imaging, the fluorescence signals were erased by TCEP, allowing the quantification of the second molecular target in the same set of cells. Through cycles of labeling, imaging and cleavage, XRCC1, golgin-97, TFIIH p89, oxphos complex V inhibitor protein, nuclear antigens, vimentin and nucleolin were unambiguously detected in nucleus, golgi, mitochondria or nucleolus (FIG. 6, panels B-H). The distribution patterns and expression levels of the protein targets obtained in this cyclical immunofluorescence approach were consistent with those in standard immunofluorescence (FIG. 6, panels I-P). The results indicated that highly multiplexed protein profiling in single cells may be achieved using cleavable fluorescent antibodies.

In general, cleavable fluorescent antibodies may be applied for iterative protein profiling on the single-cell level. The number of proteins that can be detected in individual cells may depend on factors including the number of immunofluorescence cycles and the number of proteins analyzed in each cycle. It has been determined that TCEP may efficiently remove fluorophores tethered to a probe with a linker molecule within about 30 minutes. In the case of a protein-based target, the antigenicity of the probe is retained after incubating for at least 24 hours. This suggests that the number of staining, imaging and cleavage cycles may be further increased by a significant amount. With fluorophores of different colors (i.e., different excitation/emission profiles), four, five or more varied protein targets may be quantified in a single immunofluorescence cycle. Moreover, fluorophores with multispectral properties (Guo, J. et al., Proc. Natl. Acad. Sci. U.S.A. 2011, 108, 3493; Dai, et al., Angew. Chem. Int. Ed. Engl. 2011, 50, 5105; Wang, et al., Angew. Chemie Int. Ed. 2012, 51, 7176) may allow more proteins to be analyzed in a single cycle using hyperspectral imaging techniques (Garini, et al., Cytometry. A 2006, 69, 735). Therefore, embodiments of the present disclosure using cleavable fluorescent antibodies may enable the detection of over one hundred protein targets in a single cell environment.

Figure 7:
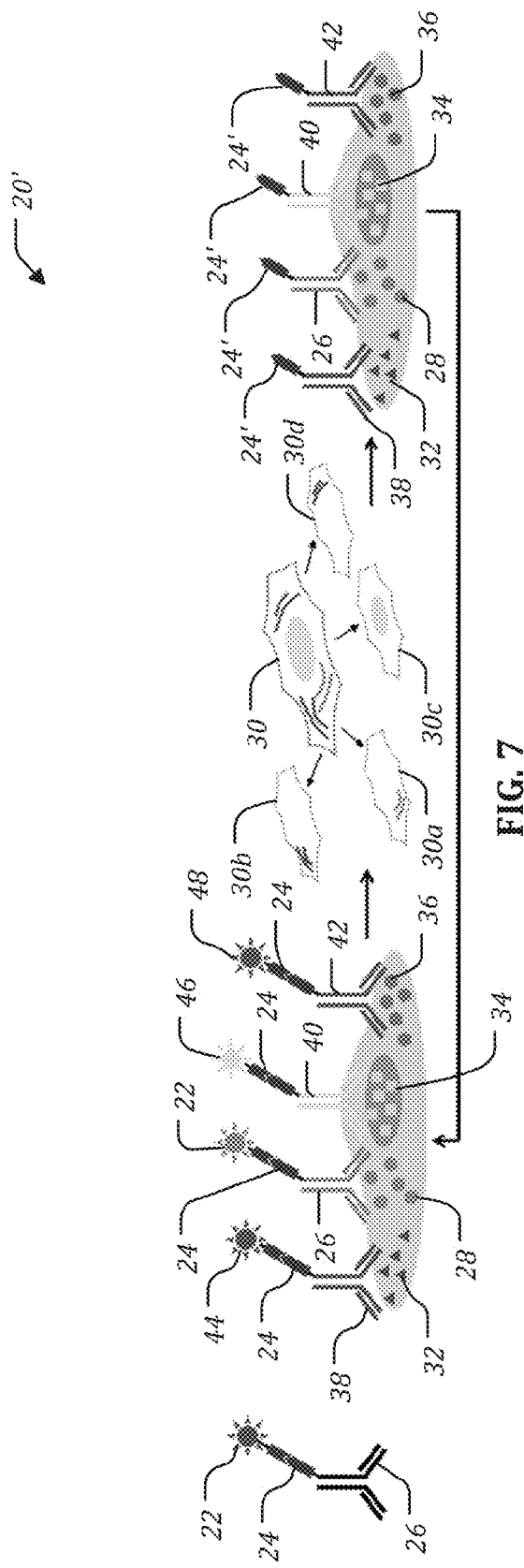
FIG. 7 is a schematic illustration of multiplexed immunofluorescence with cleavable fluorescent antibodies. Protein targets in fixed cells may be recognized by cleavable fluorescent antibodies. After imaging, the fluorophores may be removed by cleavage of the linker. Through cycles of staining, imaging and cleavage, a large number of different protein targets may be quantified in individual cells.

For example, FIG. 7 illustrates an embodiment of a system 20' for multiplexed iterative immunofluorescence using chemically cleavable fluorescent antibodies. The system 20' can include the first fluorophore 22, the cleavable linker 24 and the first antibody 26. As in system 20 in FIG. 1, the linker 24 may be used to tether the fluorophore 22 to the antibody 26. In one aspect, the first antibody 26 may selectively bind the first population 28 of protein targets in a cell 30. Similarly, the second population 32, third population 34 and fourth population 36 may be targeted with antibody 38, antibody 40 and antibody 42, respectively. The antibody 38 may tethered to a fluorophore 44 with the linker 24. In one aspect, the fluorophore 44 may be different from the fluorophore 22. Similarly, the antibody 40 may tethered to a fluorophore 46 with the linker 24 and the antibody 42 may tethered to a fluorophore 48 with the linker 24.

Each of the fluorophores selected for use in a system, such as the system 20', may be unique in order to differentiate between target molecules during fluorescence imaging. However, each of the linkers used to tether the fluorophores to their respective antibodies may be the same or similar. Accordingly, each of the linkers may be cleaved with a single chemical treatment. With continued reference to FIG. 7, multichannel (multiplexed) fluorescence imaging may be performed for the cell 30. Quantitative or qualitative analysis of the population 28, the population 32, the population 34 and the population 36 in the cell 30 may be facilitated by the presence of the respective fluorophore linked antibodies. The arrow between cell 30 and cell 30a indicates that the population 28 may be distinguished by exciting only the fluorophore 22. Similarly, the arrow between cell 30 and cell 30ba indicates that the population 32 may be distinguished by exciting only the fluorophore 44. Finally, the arrow between cell 30 and cell 30c indicates that the population 34 may be distinguished by exciting only the fluorophore 46, and the arrow between cell 30 and cell 30d indicates that the population 36 may be distinguished by exciting only the fluorophore 48.

Following fluorescence imaging, each of the linkers 24 may be chemically treated, thereby cleaving the respective fluorophore from their corresponding antibodies. As shown for system 20 in FIG. 1, portions 24' of the linkers 24 in system 20' may remain tethered to the antibodies following cleavage. As indicated by the arrows in FIG. 7, successive rounds of target binding, imaging and cleavage may be performed on other target protein populations within the cell 30, thereby allowing for iterative rounds of multiplexed fluorescence imaging.

In some embodiments, the chemically cleavable fluorophores described herein may also be applied in other areas beyond protein quantification, such as DNA or RNA in situ hybridization and metabolic analysis. These extended applications may provide a highly multiplexed imaging platform that integrates DNA, RNA, protein and metabolic analysis at the optical resolution in single cells, which may bring new insights into systems biology, cell heterogeneity studies, molecular diagnosis and cellular targeted therapy. In some embodiments, azide-based chemically cleavable linkers may be prepared for targeting nucleic acid materials including DNA and RNA.

Turning to FIG. 8, multiplexed DNA fluorescence in situ hybridization (FISH) may be achieved with cleavable fluorescent probes. A DNA-based probe 50 may be prepared by conjugating a fluorophore 52 to an oligonucleotide (e.g., a PCR product) 54 with a cleavable linker 56. Thereafter, different genomic regions 58 in fixed cells 60 may be hybridized with cleavable fluorescent PCR product probes 50. After imaging, the fluorophores 52 may be removed by cleavage of the linkers 56. As in the system 20, a portion 56' of the linker may remain conjugated to the oligonucleotide 54. Through cycles of staining, imaging and cleavage, a large number of different genomic regions 58 can be quantified in individual cells 60.

Similarly, FIG. 9 shows an example of multiplexed RNA FISH with cleavable fluorescent probes 60 including a fluorophore 62 conjugated to an oligonucleotide 64 via a cleavable linker 66. RNAs 68 in fixed cells 70 are hybridized with the cleavable fluorescent oligonucleotide probes 60. After imaging, the fluorophores 62 are removed by cleavage of the linker 66. As in the system 20, a portion 66' of the linker may remain conjugated to the oligonucleotide 64. Through cycles of staining, imaging and cleavage, a large number of different RNAs 68 can be quantified in individual cells 70.

Figures 10A, 10B, 10C:
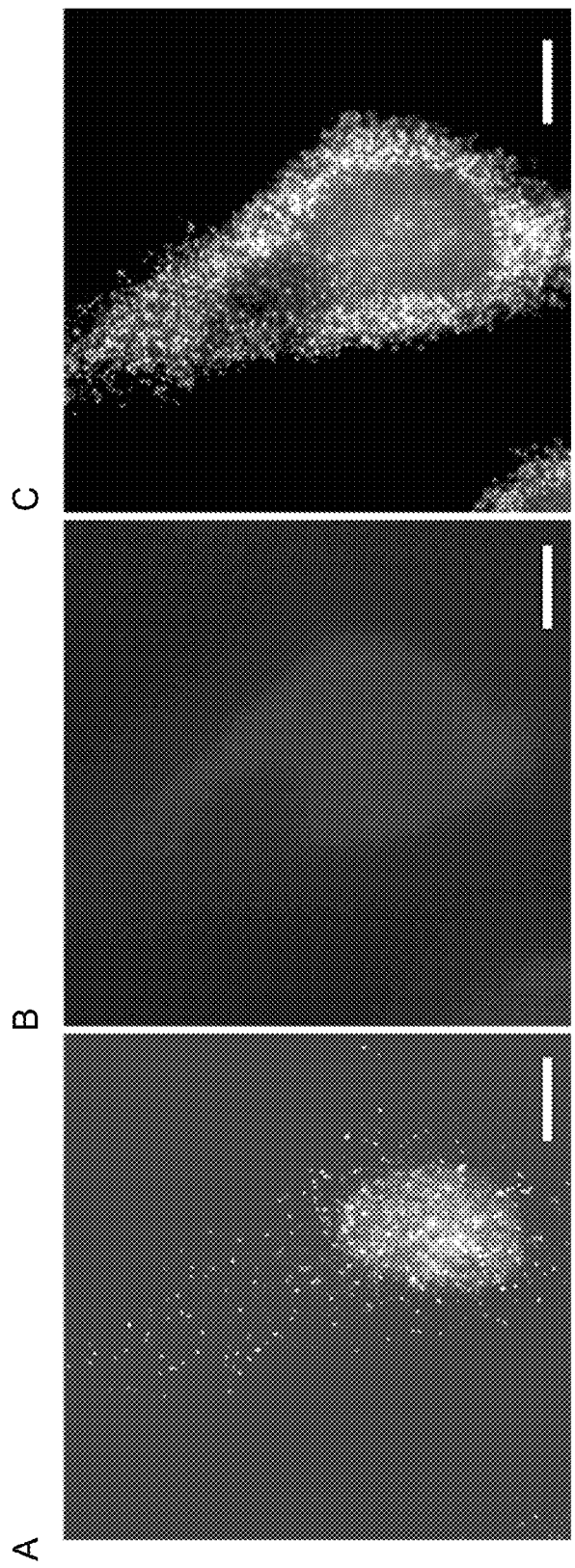
FIGS. 10A-10C show optical fluorescence image of mRNA quantification in HeLa cells.

To demonstrate the feasibility of performing cyclical RNA FISH with cleavable fluorescent probes, GAPDH and ACTB mRNA were labeled in two subsequent cycles. First, HeLa cells were incubated with cleavable fluorescent oligonucleotides, which have complimentary sequences of GAPDH mRNA (FIG. 10A). Upon treatment with TCEP, the fluorophores tethered to the oligonucleotides through the cleavable linker were efficiently removed by chemical cleavage of the linker (FIG. 10B). In the second cycle, ACTB mRNA molecules were stained with their corresponding fluorescent RNA FISH probes (FIG. 10C). These results demonstrated that multiplexed cyclical RNA FISH may be achieved by using cleavable fluorescent probes.

In some embodiments, a fluorescent probe may include multiple cleavable linkers. In one aspect, multiple cleavable linkers may be used to further increase the fluorophore removal efficiency under cleavage conditions similar to those used for probes including a single cleavable linker. Accordingly, cleavable fluorophores with multiple cleavable linkers conjugated to one fluorophore were designed and synthesized. These cleavable fluorophores may be conjugated to any probe (e.g., antibodies, oligonucleotides, PCR products, peptide nucleic acids and the like) using a chemical synthesis approach similar to that described herein. To efficiently remove the fluorophore from the probes, only one of several cleavable linkers is required to be cleaved. Therefore, the fluorophore removal efficiency may be increased.

Figure 11:
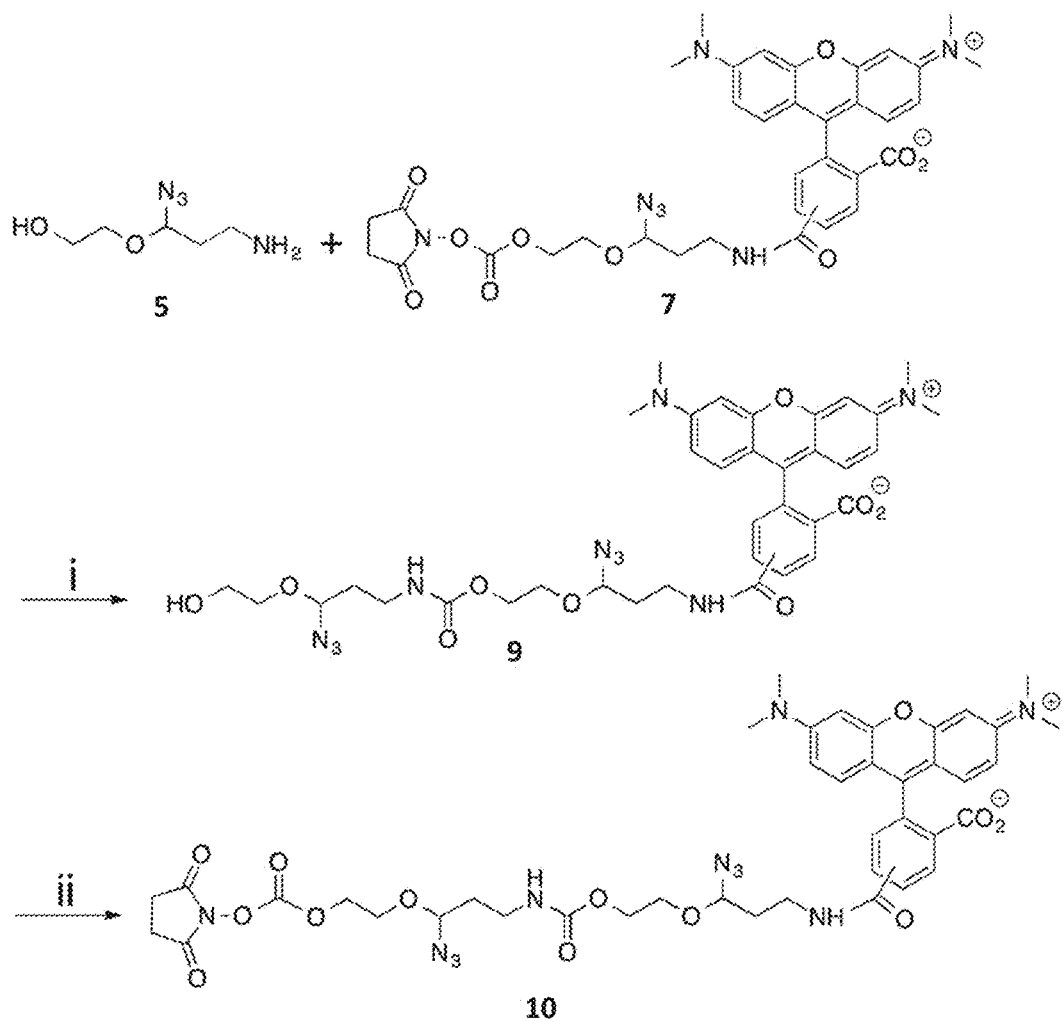
FIG. 11 is a scheme illustrating the chemical synthesis of 2-linker cleavable TAMRA.

In one example, to synthesize a cleavable fluorophore having multiple linkers, two cleavable linkers may be coupled to a fluorophore sequentially as illustrated in FIG. 11. Alternatively or additionally, a plurality of cleavable linkers can be coupled together and then conjugated to a fluorophore to form the cleavable fluorophore having multiple linkers. Still other methods of synthesis may be possible.

In some embodiments, an azide based linker may have the generic structure:

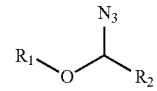

where $R_1$ is linkage between one of a probe and a detectable marker (e.g., a fluorophore) and $R_2$ is a linkage between the other of the probe and the detectable marker. In one aspect, a sulfur atom may be substituted for the oxygen atom in the above linker structure. In another aspect, other phosphine-based reducing reagents, dithiothreitol (DTT) and other like reducing reagents may be used as the cleavage reagent.

In some embodiments, an alternative (or additional) cleavable linker may be substituted for an azide-based linker as described herein. For example, disulfide bond based linkers can also be cleaved by TCEP. Suitable cleavable linkers may include structures cleaved by enzymes, nucleophiles, electrophiles, reducing reagents, oxidizing reagents, photo-irradiation, metal catalysis, and the like. Further examples of suitable linkers and cleavage mechanisms are described by Milton et al. (U.S. Pat. No. 7,414,116) and by Leriche et al. (Leriche, et al., Bioorg. Med. Chem., 2012, 20, 571-582).

EXAMPLES

With respect to immunofluorescence experiments involving antibody-linked fluorophores for detection of target proteins, chemicals and solvents were purchased and used directly without further purification, unless otherwise noted. $^1$H-NMR and $^{13}$C-NMR were acquired with a 400 MHz nuclear magnetic resonance (NMR) spectrometer. Chemical shifts are reported in parts per million (ppm) downfield from tetramethylsilane (TMS). Data are reported as follows: chemical shift, multiplicity: singlet (s), doublet (d), triplet (t), multiplet (m), coupling constants J in Hz, and integration.

Figure 12:
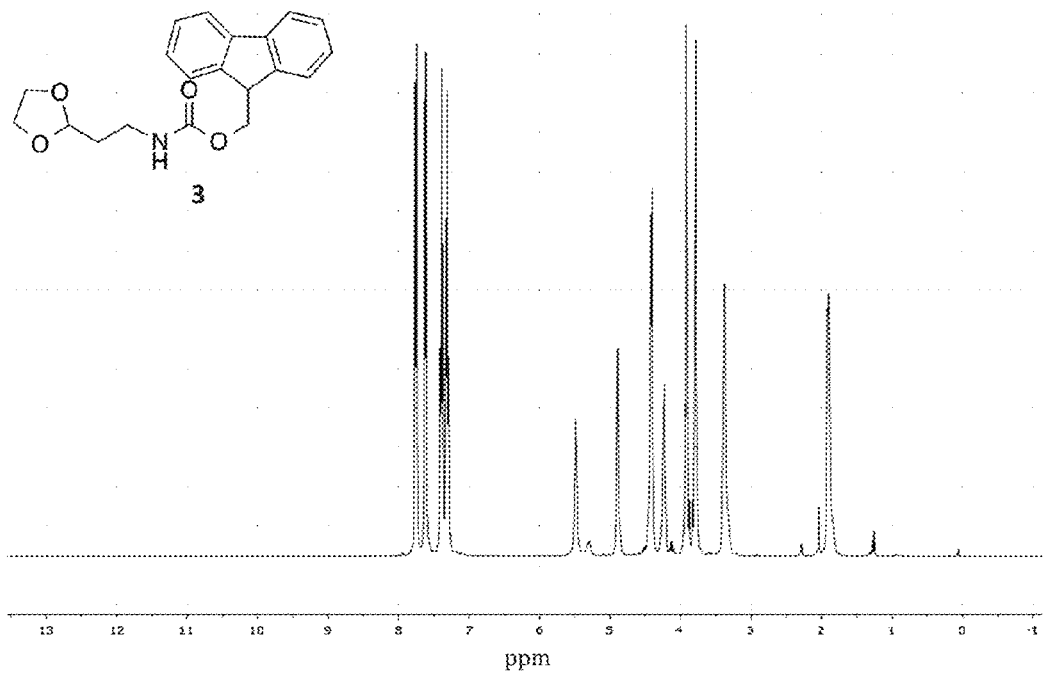
FIG. 12 is an $^1$H NMR spectrum for compound 1 (400 MHz, CDCl$_3$).
Figure 13:
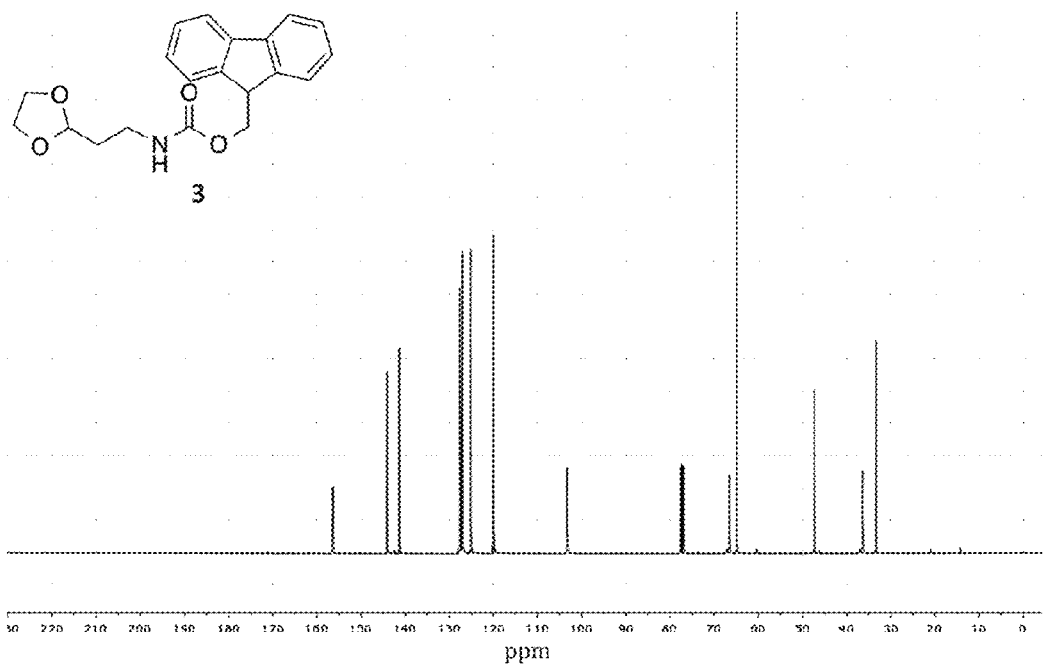
FIG. 13 is a $^{13}$C NMR spectrum for Compound 1 (100 MHz, CDCl$_3$).

For the synthesis of cleavable TAMRA conjugated antibodies, (9H-fluoren-9-yl)methyl (2-(1,3-dioxolan-2-yl)ethyl)carbamate (FIG. 2, compound 3) was prepared by stirring a solution of 9-fluorenylmethyl chloroformate (6.6 g; 25.6 mmol) in 40 ml of ether. The solution was cooled in an ice bath. Commercially available 2-(aminoethyl)-1,3-dioxolane (2 g; 17.0 mmol) was slowly added, and the reaction mixture was stirred at 0° C. for 10 minutes and then at room temperature for 30 minutes. After complete evaporation of ether from the reaction mixture, the resulting residue was purified by flash column chromatography using ethyl acetate/hexane (1:2 to 1:1) to afford compound 3 as a white solid (5.67 g; 97% yield). With reference to FIG. 12, $^1$H NMR (400 MHz, CDCl$_3$) δ 7.75 (d, J=7.5 Hz, 2H), 7.62 (d, J=7.5 Hz, 2H), 7.39 (t, J=7.5 Hz, 2H), 7.31 (d, J=7.5 Hz, 2H), 4.90 (t, J=4.5 Hz, 1H), 4.41 (d, J=7.1 Hz, 2H), 4.24 (t, J=8 Hz, 1H), 3.96-3.88 (m, 2H), 3.83-3.75 (m, 2H), 3.38 (t, J=6.2 Hz, 2H), 1.90 (m, 2H). With reference to FIG. 13, $^{13}$C NMR (100 MHz, CDCl$_3$) δ 156.43, 144.10, 141.31, 127.67, 127.05, 125.13, 119.99, 103.31, 66.56, 64.88, 47.33, 36.40, 33.36; HRMS (ESI, m/z) calculated for C$_{20}$H$_{21}$NO$_4$ [(M+Na)$^+$]: 362.1368, found: 362.1360.

Figure 14:
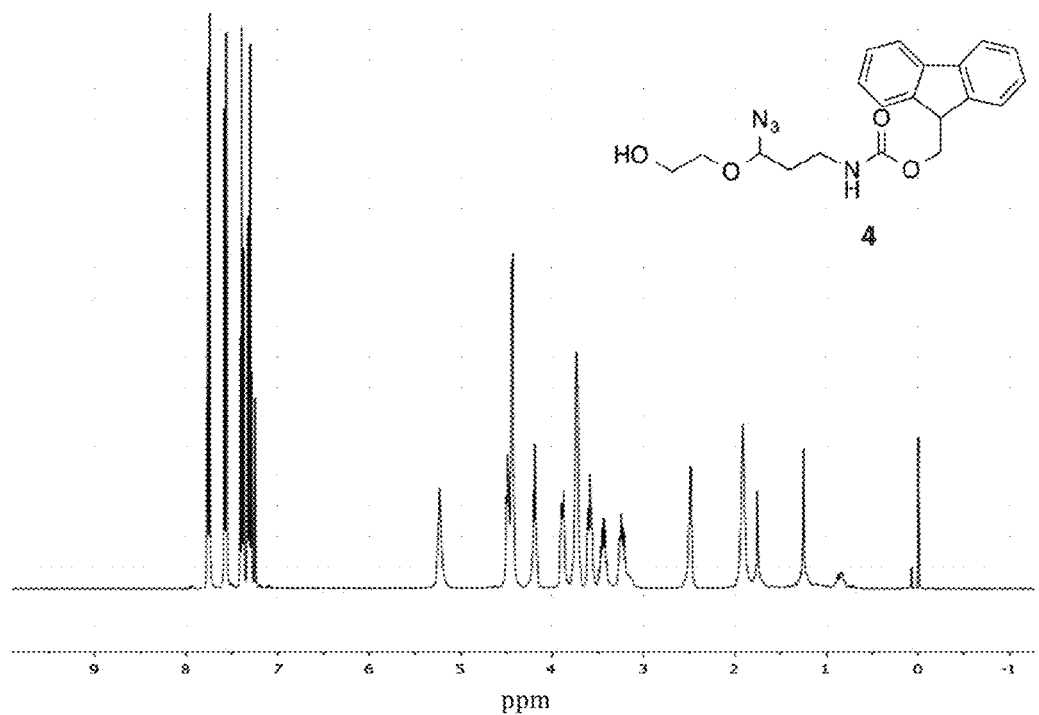
FIG. 14 is an $^1$H NMR spectrum for compound 2 (400 MHz, CDCl$_3$).
Figure 15:
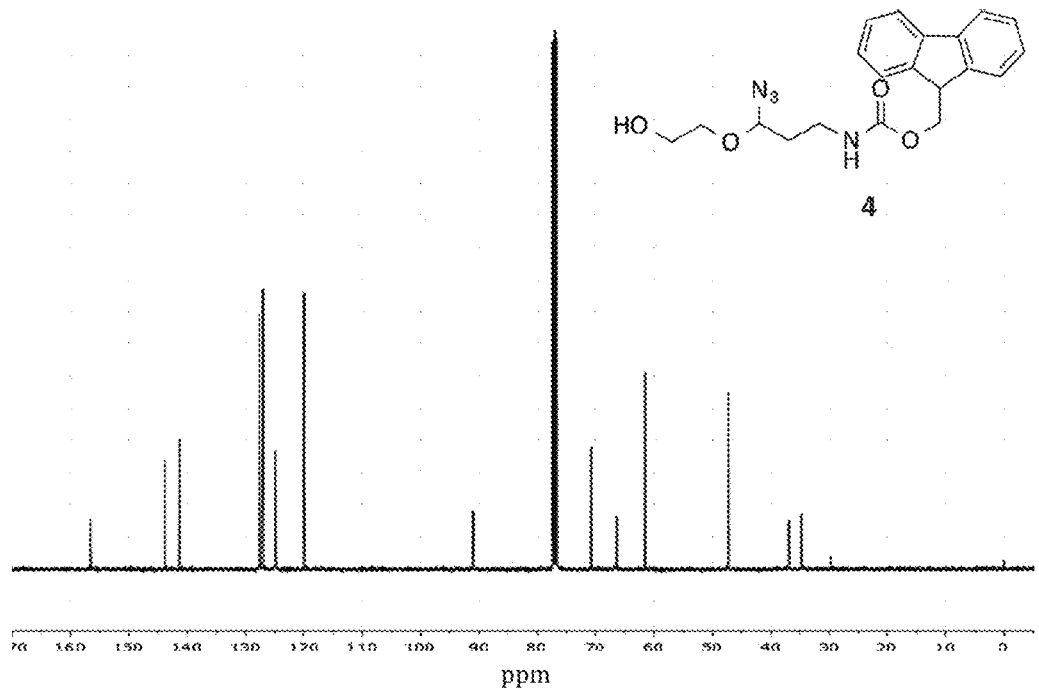
FIG. 15 is a $^{13}$C NMR spectrum for compound 2 (100 MHz, CDCl$_3$).

For the preparation of (9H-fluoren-9-yl)methyl (3-azido-3-(2-hydroxyethoxy)propyl)carbamate (FIG. 2, compound 4), a stirred solution of compound 3 (1.0 g; 2.95 mmol) in 20 ml CH$_2$Cl$_2$ was cooled at −78° C. in a dry ice/acetone bath under nitrogen atmosphere. To this solution azidotrimethylsilane (0.8 ml; 6.11 mmol) and Tin (IV) chloride (1 M solution in CH$_2$Cl$_2$; 150 μl) were added. Then the reaction mixture was warmed to room temperature over 15 hours. After adding CH$_2$Cl$_2$ (100 ml) to the reaction mixture, the organic layer was washed with water and dried over anhydrous Na$_2$SO$_4$. After evaporation of CH$_2$Cl$_2$ from the reaction mixture, the residue was purified by flash column chromatography using ethyl acetate/hexane (1:1) to afford compound 4 as a colorless liquid (495 mg; 44% yield). With reference to FIG. 14, $^1$H NMR (400 MHz, CDCl$_3$) δ 7.75 (d, J=7.5 Hz, 2H), 7.57 (d, J=7.4 Hz, 2H), 7.39 (td, J=7.5, 1.1 Hz, 2H), 7.30 (td, J=7.4, 1.2 Hz, 2H), 4.49 (t, J=6 Hz, 1H), 4.43 (d, J=4 Hz, 2H), 4.19 (t, J=6.6 Hz, 1H), 3.91-3.87 (m, 1H), 3.78-3.69 (m, 2H), 3.61-3.56 (m, 1H), 3.49-3.40 (m, 1H), 3.29-3.20 (m, 1H), 1.92 (m, 2H). With reference to FIG. 15, $^{13}$C NMR (100 MHz, CDCl$_3$) δ 156.60, 143.87, 141.31, 127.68, 127.04, 124.93, 119.95, 91.01, 70.74, 66.46, 61.53, 47.26, 36.88, 34.73; HRMS (APCI, m/z) calculated for C$_{20}$H$_{22}$N$_4$O$_4$ [(M−N$_2$+H)$^+$]: 355.1658, found: 355.1648.

Figure 16:
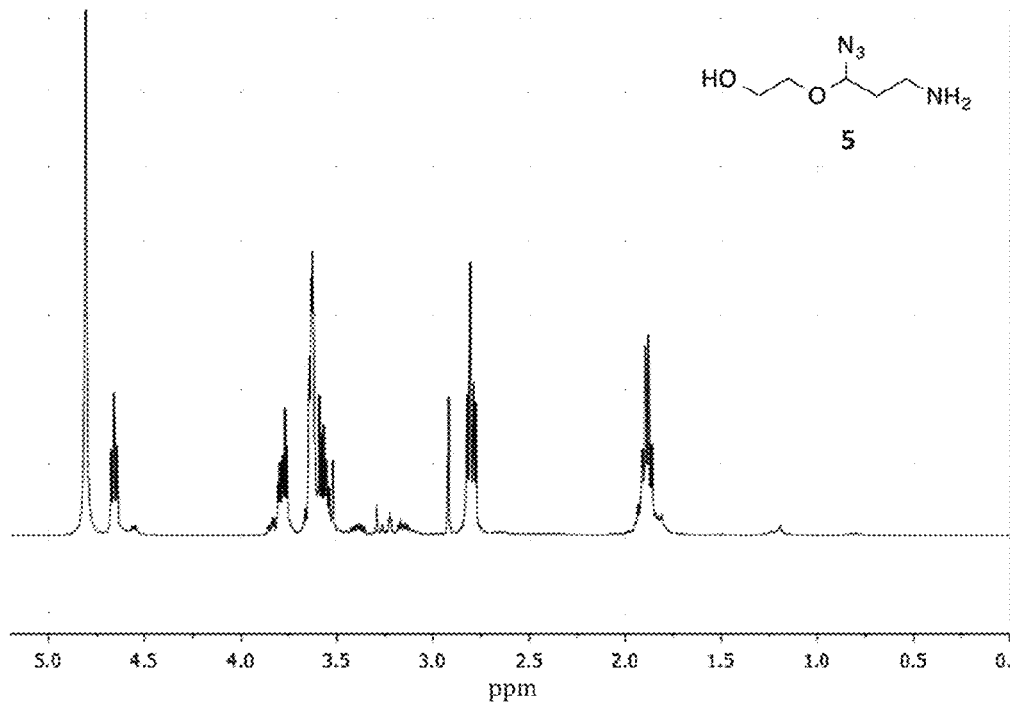
FIG. 16 is an $^1$H NMR spectrum for compound 3 (400 MHz, CD$_3$OD).
Figure 17:
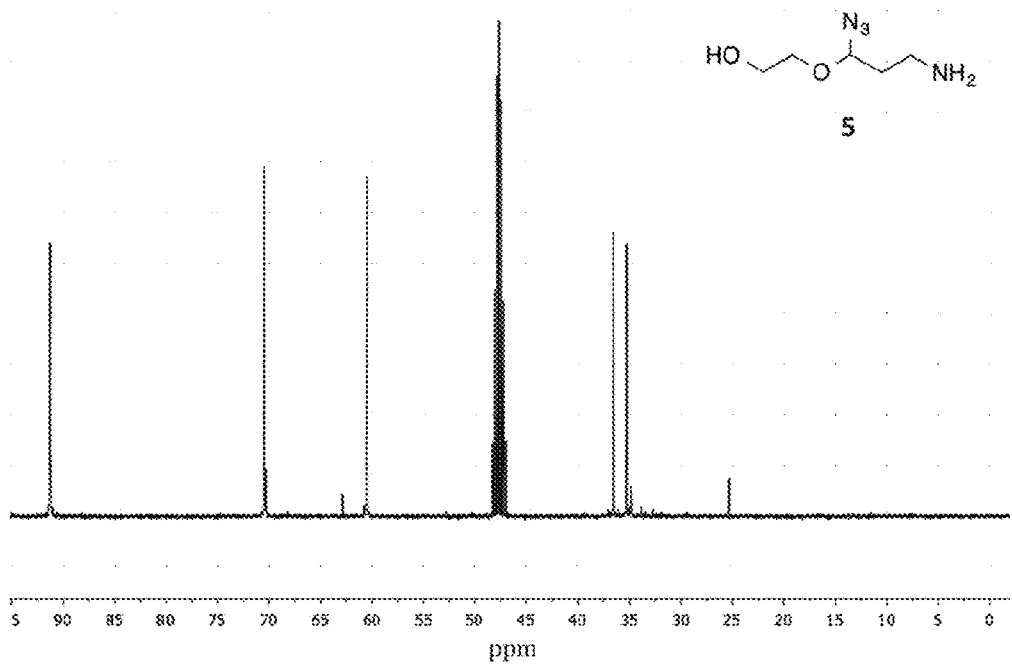
FIG. 17 is a $^{13}$C NMR spectrum for compound 3 (100 MHz, CD$_3$OD).

For the preparation 2-(3-amino-1-azidopropoxy)ethanol (FIG. 2, compound 5), piperidine (0.3 ml; 3.03 mmol) was added to a stirred solution of compound 4 (300 mg; 0.79 mmol) in 3 ml CH$_2$Cl$_2$. The reaction mixture was stirred at room temperature for 30 minutes. After completion of the reaction most of the solvent and piperidine were dried under vacuum. The residue was purified by flash column chromatography using ethyl acetate/hexane (1:1) and then 5% NH$_4$OH in methanol/dichloromethane (1:1) to afford compound 3 as a brown oil (100 mg; 80% yield). With reference to FIG. 16, $^1$H NMR (400 MHz, CD$_3$OD) δ 4.66 (t, J=5.9 Hz, 1H), 3.88-3.70 (m, 1H), 3.70-3.53 (m, 3H), 2.80 (t, J=6.7 Hz, 2H), 2.00-1.84 (m, 2H). With reference to FIG. 17, $^{13}$C NMR (100 MHz, CD$_3$OD) δ 91.28, 70.50, 60.50, 36.55, 35.26; HRMS (FAB, m/z) calculated for C$_5$H$_{12}$N$_4$O$_2$ [(M+H)$^+$]: 161.1038, found: 161.1037.

Figure 18:
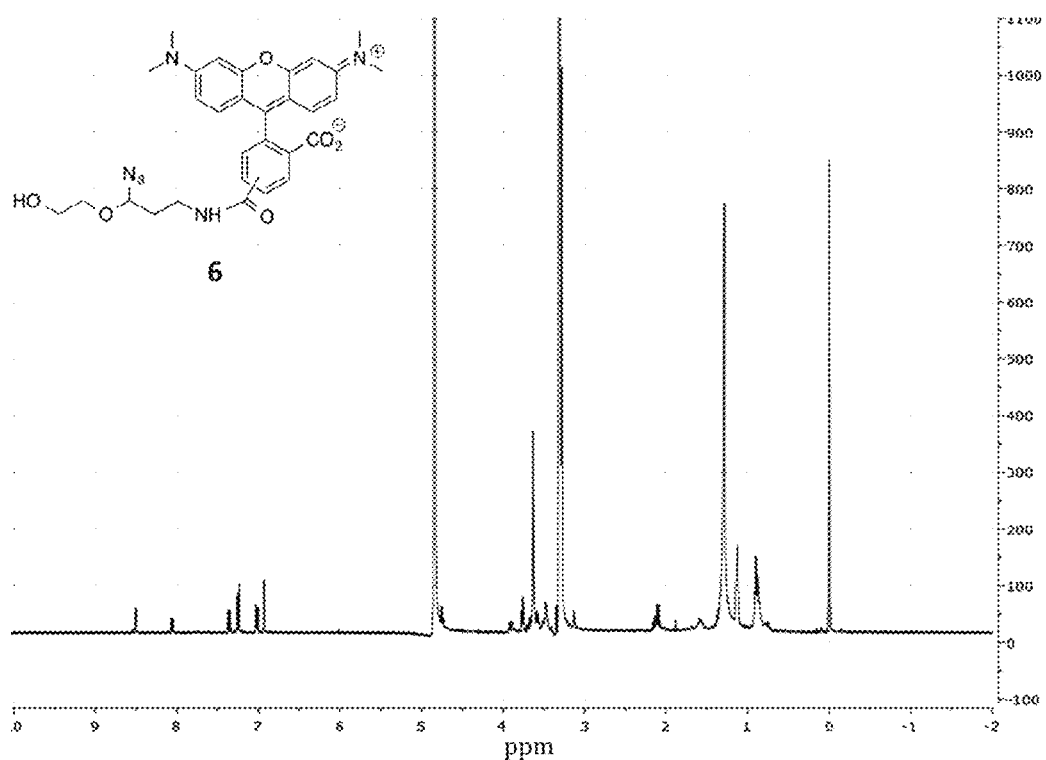
FIG. 18 is an $^1$H NMR spectrum for compound 4 (400 MHz, CD$_3$OD).

For the preparation of Azido-TAMRA (FIG. 2, compound 6), 1 M NaHCO$_3$ (100 μl) was added to a stirred solution of compound 5 (1 mg; 6.24 μmol) in anhydrous DMF (860 μl). The solution was stirred at room temperature for 5 minutes. TAMRA NHS (N-hydroxysuccinimide) ester (1 mg; 1.89 μmol) in 40 μl of anhydrous DMF was added. The reaction mixture was stirred at room temperature for around 6 hours. After completion the reaction DMF was removed completely under vacuum. The crude product was purified by a preparative silica gel TLC plate by using CH$_3$OH/CH$_2$Cl$_2$ (1:2) to afford compound 6 as a red solid. With reference to FIG. 18, $^1$H NMR (400 MHz, CD$_3$OD) δ 8.50 (s, 1H), 8.06 (d, J=6 Hz, 1H), 7.36 (d, J=8 Hz, 1H), 7.25 (d, J=9.5 Hz, 2H), 7.02 (dd, J=9.5, 2.4 Hz, 2H), 6.93 (d, J=2.4 Hz, 2H), 4.74 (t, J=6 Hz, 1H), 3.92-3.89 (m, 1H), 3.76 (t, J=4.7 Hz, 2H), 3.71-3.67 (m, 1H), 3.28 (s, 12H), 3.13 (t, J=6.7 Hz, 2H), 2.16-2.08 (m, 2H); HRMS (APCI, m/z) calculated for C$_{30}$H$_{32}$N$_6$O$_6$ [(M+H)$^+$]: 573.2462, found: 573.2456.

For the preparation of Azido-TAMRA NHS ester (FIG. 2, compound 7), DSC (N,N'-disuccinimidyl carbonate) (2 mg; 7.8 μmol) and triethylamine (1.1 μl; 7.9 μmol) were added to a stirred solution of compound 6 in anhydrous DMF (400 μl). The reaction mixture was stirred for 10 hours. After completion of the reaction, most of the DMF was removed under vacuum. After adding 30 ml of CH$_2$Cl$_2$, the organic layer was washed with water, dried over anhydrous Na$_2$SO$_4$ and evaporated under vacuum to afford compound 7 as a red solid. The product was used directly for antibody labeling.

For the preparation of azido-TAMRA conjugated antibodies (FIG. 2, compound 8), antibodies (1 mg/ml) were dissolved in 1× phosphate buffered saline (pH=7.4) and compound 7 was dissolved in anhydrous DMF (500 μl). Sodium bicarbonate aqueous solution (1M, 2 μl) and compound 7 (1 μl) were added to a solution of an antibody (20 μl). The reaction mixture was incubated at room temperature for 15 min. Subsequently, the azido-TAMRA conjugated antibodies were purified by size exclusion chromatography using commercially available packing material. Absorbance spectra of azido-TAMRA conjugated antibodies were obtained in 1× phosphate buffered saline (pH=7.4). The labeling number of azido-TAMRA conjugated antibodies was determined with equation 1:

$$N_L = \frac{A_{TAMRA} \times \varepsilon_{Ab}}{(A_{280} - \alpha \times A_{TAMRA}) \times \varepsilon_{TAMRA}} \quad \text{(Eq. 1)}$$

where $N_L$ is the number of TAMRA moieties on each antibody molecule, $A_{280}$ is absorption of the azido-TAMRA conjugated antibody at 280 nm, $A_{TAMRA}$ is absorption of the TAMRA labeled antibody at 520 nm, $\varepsilon_{Ab}$ and $\varepsilon_{TAMRA}$ are the molar extinction coefficient of the antibody (203,000 cm$^{-1}$M$^{-1}$) and TAMRA (80,000 cm$^{-1}$M$^{-1}$), respectively, and α is defended as the ratio of absorption of TAMRA at 280 nm and 520 nm (0.36).

Antibodies with cleaved TAMRA:azido-TAMRA conjugated antibodies were incubated with 100 mM TCEP at 37° C. for 30 minutes, purified by size exclusion chromatography using commercially available packing material and characterized by absorption spectrometry.

Multiplex immunofluorescence using azido-TAMRA conjugated antibodies included cell culture, cell fixation, labeling of microtubules and cyclical immunofluorescence. For cell culture, HeLa CCL-2 cells were maintained in Dulbecco's modified Eagle's Medium (DMEM) supplemented with 10% fetal bovine serum, 100 U/mL penicillin and 100 g/mL streptomycin in a humidified atmosphere at 37° C. with 5% CO$_2$. Cells were plated on chambered coverglass (0.2 ml medium/chamber) and allowed to reach 60% confluency in 1-2 days.

For cell fixation, cultured HeLa CCL-2 cells were fixed with 4% formaldehyde at 37° C. for 15 min, permeabilized with 0.2% (vol/vol) Triton X-100 at room temperature for 15 min, and subsequently blocked in a blocking buffer (1%

(wt/vol) bovine serum albumin, 0.1% (vol/vol) Triton X-100, 10% (vol/vol) normal goat serum) at room temperature for 1 h.

For the labeling of microtubules, fixed and blocked HeLa CCL-2 cells were incubated with or without 100 mM TCEP at 37° C. for 24 hours. After incubation with 5 μg/mL rat anti-α-tubulin at room temperature for 1 hour, cells were incubated with 10 μg/mL azido-TAMRA conjugated goat anti-rat IgG or Alexa 488 labeled goat anti-rat IgG at room temperature for 1 h. Stained cells in 2× saline-sodium citrate buffer (300 mM sodium chloride, 30 mM trisodium citrate, pH=7.0) were imaged under an epifluorescence microscope equipped with 40× objective. Subsequently, cells were incubated with 100 mM TCEP at 37° C. for 30 minutes, and then imaged again. Images were captured using a CCD camera and commercially available imaging software using appropriate filters.

For cyclical immunofluorescence, fixed and blocked HeLa CCL-2 cells were incubated with primary antibodies at their optimal concentrations at room temperature for 1 hour and subsequently with 10 μg/mL primary antibody species-specific goat IgG conjugated to azido-TAMRA at room temperature for 1 h. After imaging, stained cells were incubated with 100 mM TCEP at 37° C. for 30 minutes, followed by the next immunofluorescence cycle. 5 μg/mL rat anti-α-tubulin, 1:200 diluted mouse anti-XRCC1, 1 μg/mL mouse anti-golgin-97, 5 μg/mL rabbit anti-TFIIH p89, 5 μg/mL mouse anti-OxPhos complex V inhibitor protein, pre-diluted human anti-nuclear antigen antibody, 5 μg/mL chicken anti-vimentin and 5 μg/mL mouse anti-nucleolin antibody were used sequentially as primary antibodies. For control experiments, fixed and blocked HeLa CCL-2 cells were incubated with primary antibodies at their optimal concentrations at room temperature for 1 h, and subsequently with 10 μg/mL primary antibody species-specific goat IgG conjugated to Alexa 488 at room temperature for 1 h. All stained cells in 2× saline-sodium citrate buffer were imaged under an epifluorescence microscope equipped with a 40× objective. Images were captured using a CCD camera and commercially available imaging software using appropriate filters.

For RNA FISH experiments (FIG. 9), commercially available amino modified RNA FISH probes were dissolved in water (1.25 μg/μl) and compound 7 was dissolved in anhydrous DMF (20 μg/μl). To a solution of RNA FISH probes (40 μl) were added sodium bicarbonate aqueous solution (1M, 10 μl) and compound 7 (50 μl). The reaction mixture was incubated at room temperature overnight. After ethanol precipitation, the labeled probes were purified by reserve phase HPLC using a C18 column with a gradient of 0.1 M triethylamonium acetate and acetonitrile. mRNA staining was performed following using a commercially available kit. After imaging, stained cells were incubated with 100 mM TCEP at 37° C. for 30 minutes, followed by a subsequent RNA FISH cycle.

The synthesis of probes with multiple cleavable linkers was accomplished in several steps as illustrated in FIG. 11. For the preparation of azido-azido-TAMRA (compound 9), 1 M NaHCO$_3$ (100 μl) was added to a stirred solution of compound 5 (1 mg; 6.24 μmol) in anhydrous DMF (860 μl). The solution was then stirred at room temperature for 5 minutes. Compound 7 (1 mg; 1.40 μmol) in 40 μl of anhydrous DMF was added. The reaction mixture was stirred at room temperature for around 6 hours. After completion the reaction DMF was removed completely under vacuum. The crude product was purified by a preparative silica gel TLC plate by using CH$_3$OH/CH$_2$Cl$_2$ (1:2) to afford compound 9 as a red solid. NMR was performed to confirm the identity of compound 9: $^1$H NMR (400 MHz, CD$_3$OD) δ 8.50 (s, 1H), 8.06 (d, J=6 Hz, 1H), 7.36 (d, J=8 Hz, 1H), 7.25 (d, J=9.5 Hz, 2H), 7.02 (dd, J=9.5, 2.4 Hz, 2H), 6.93 (d, J=2.4 Hz, 2H), 4.74 (t, J=6 Hz, 2H), 3.92-3.89 (m, 2H), 3.76 (m, 4H), 3.71-3.67 (m, 2H), 3.28 (s, 12H), 3.13 (t, J=6.7 Hz, 4H), 2.16-2.08 (m, 4H).

For the preparation of azido-azido-TAMRA NHS ester (Compound 10), DSC (N,N'-disuccinimidyl carbonate) (2 mg; 7.8 μmol) and triethylamine (1.1 μl; 7.9 μmol) were added to a stirred solution of compound 9 in anhydrous DMF (400 μl). The reaction mixture was stirred for 10 hours. After completion of the reaction, most of the DMF was removed under vacuum. After adding 30 ml of CH$_2$Cl$_2$, the organic layer was washed with water, dried over anhydrous Na$_2$SO$_4$ and evaporated under vacuum to afford compound 8 as a red solid.

Figures 19A, 19B, 19C:
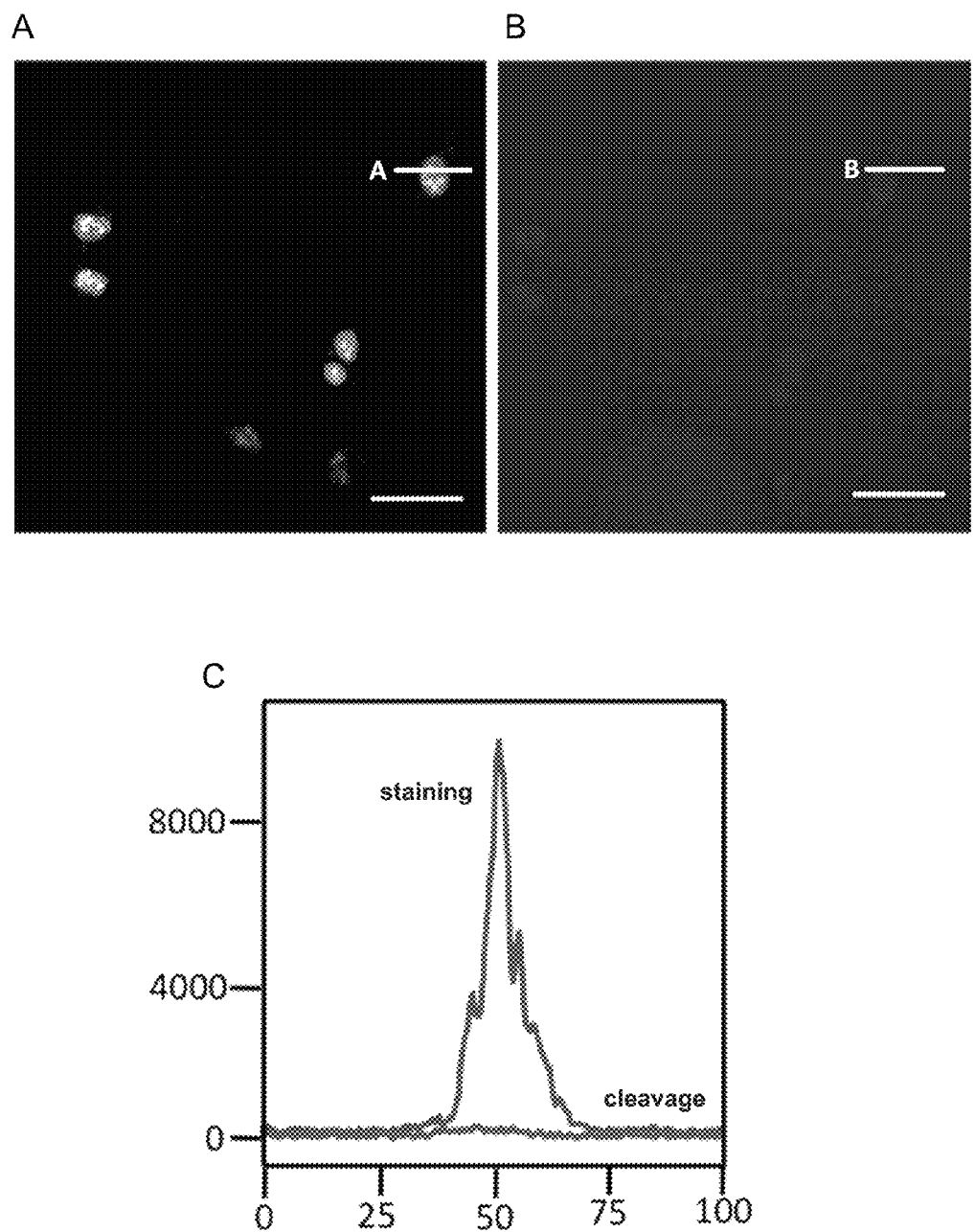
FIGS. 19A-19C are data illustrating the results of TCEP treatment of fluorescence probes including multiple cleavable linkers.

To assess the fluorophore removal efficiency of azido-azido TAMRA labeled antibodies, HeLa cells were incubated with rabbit anti-Ki67 and subsequently with azido-azido TAMRA conjugated goat anti-rabbit (FIG. 19A). After fluorophore cleavage with 100 mM TCEP at 37° C. for 30 minutes, almost all the fluorescence signals from the labeled Ki67 were erased (FIG. 19B). The on/off ratio between the signals before and after the TCEP treatment was over 50:1 (FIG. 19C). These results demonstrated that under the same cleavage condition, fluorophores conjugated with multiple cleavable linkers have improved fluorophore removal efficiency as compared with fluorophores coupled with only one linker.

The schematic flow chart shown in the figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the figures are provided to explain the logical steps of the method and are understood not to limit the scope of the method. Although various arrow types and line types may be employed, they are understood not to limit the scope of the corresponding methods. Indeed, some arrows or other connectors may be used to indicate only the logical flow of the methods. For instance, an arrow may indicate a waiting or monitoring period of unspecified duration between enumerated steps of the depicted method. Additionally, the order in which a particular method occurs may or may not strictly adhere to the order of the corresponding steps shown.

The present invention has been described in terms of one or more preferred embodiments, and it should be appreciated that many equivalents, alternatives, variations, and modifications, aside from those expressly stated, are possible and within the scope of the invention.

Each reference identified in the present application is herein incorporated by reference in its entirety.

What is claimed is:

1. A system for iterative in situ fluorescence detection of biological molecules, comprising:
   a multi-nucleotide or antibody probe; and
   a fluorophore tethered to the probe by an azide-based linker;
   wherein the azide-based linker is configured to be cleaved by tris(2-carboxyethyl)phosphine (TCEP) at a plurality of sequential TCEP-specific cleavage sites within said linker thereby cleaving the fluorophore from the multi-nucleotide or antibody probe upon exposure to TCEP, and wherein the on/off ratio between a fluorescent signal produced by said fluorophore measured before treatment with TCEP and a fluorescent signal produced by said fluorophore measured after treatment with TCEP is at least about 20:1.

2. The system of claim 1, wherein the linker is:

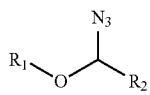

wherein $R_1$ is linkage between one of the probe and the fluorophore and wherein $R_2$ is a linkage between the other of the probe and the fluorophore.

3. The system of claim 1, wherein the multi-nucleotide or antibody probe is selected for the detection of at least one of a DNA target, an RNA target, a protein target and a small molecule target.

4. A method for iterative in situ fluorescence detection a biological molecule, comprising:
incubating a sample including a target molecule with a detection system, the detection system including a multi-nucleotide or antibody probe and a fluorophore tethered to the probe by an azide-based linker comprising a plurality of TCEP-specific cleavage sites;
exciting the incubated sample at a first wavelength;
detecting the emission of a second wavelength from the excited, incubated sample; and
contacting tris(2-carboxyethyl)phosphine (TCEP) to the excited, incubated sample, whereby the TCEP cleaves at one or more of the plurality of sequential TCEP-specific cleavage sites, thereby cleaving the fluorophore from the probe, wherein the on/off ratio between the emission of the second wavelength detected before the contacting step and an emission of the second wavelength after the contacting step is at least about 20:1.

5. The method of claim 4, further including, repeating the steps of incubating, exciting and detecting.

6. The method of claim 4, wherein the linker is:

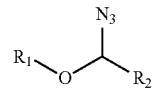

wherein $R_1$ is linkage between one of the probe and the fluorophore and wherein $R_2$ is a linkage between the other of the probe and the fluorophore.

7. The method of claim 4, wherein the probe is selected for the in situ detection of at least one of a DNA target, an RNA target, a protein target and a small molecule target.

8. The method of claim 4, further including binding the target molecule with the probe.

9. The method of claim 4, wherein the on/off ratio between a signal measured before treatment with TCEP and a signal measured after treatment with TCEP is at least about 50:1.

* * * * *

UNITED STATES PATENT AND TRADEMARK OFFICE
CERTIFICATE OF CORRECTION

PATENT NO. : 9,933,431 B2  
APPLICATION NO. : 14/820875  
DATED : April 3, 2018  
INVENTOR(S) : Jia Guo Page 1 of 1

It is certified that error appears in the above-identified patent and that said Letters Patent is hereby corrected as shown below:

In the Specification

Column 12, Line 67, "in a" should be --in 1X--.

Signed and Sealed this
Twenty-fourth Day of July, 2018

Andrei Iancu
*Director of the United States Patent and Trademark Office*